United States Patent [19]

Berger et al.

[11] 4,267,174
[45] May 12, 1981

[54] IMMUNE-STIMULATING AND CANCEROSTATIC 1-ACYL-2-CYANOAZIRIDINES

[75] Inventors: Herbert Berger, Mannheim-Kafertal; Rudi Gall, Hirschberg-Grossachsen; Wolfgang Kampe, Heddesheim; Uwe Bicker, Mannheim; Rolf Kuhn, Mannheim-Waldhof, all of Fed. Rep. of Germany

[73] Assignee: Boehringer Mannheim, GmbH, Mannheim, Fed. Rep. of Germany

[21] Appl. No.: 916,389

[22] Filed: Jun. 16, 1978

[30] Foreign Application Priority Data

Jul. 11, 1977 [DE] Fed. Rep. of Germany ....... 2731264

[51] Int. Cl.³ ................. A61K 31/395; C07D 403/06; C07D 401/06; C07D 405/06
[52] U.S. Cl. .................................. 424/244; 424/274; 424/275; 424/285; 424/273 P; 424/282; 424/250; 424/263; 424/270; 424/273 R; 260/152; 260/239 E; 260/239 EP; 260/347.8; 260/346.73; 260/326 N; 260/326.5 FL; 260/340.9 R; 549/59; 544/238; 546/275; 548/374; 548/200; 548/183; 548/309
[58] Field of Search ............. 260/239 E, 239 EP, 152; 546/275; 544/238; 424/244

[56] References Cited

FOREIGN PATENT DOCUMENTS 2528460  1/1977  Fed. Rep. of Germany ....... 260/239 E
110492 12/1974  German Democratic Rep.  260/239 E Primary Examiner—Mark L. Berch
Attorney, Agent, or Firm—Sprung, Felfe, Horn, Lynch & Kramer

[57] ABSTRACT

1-Acyl-2-cyanoaziridines of the formula

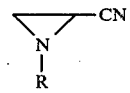

wherein
R is an acyl radical of a carboxylic, sulphonic, sulphinic, sulphenic, phosphonic or phosphoric acid,
exhibit immune-stimulating and cancerostatic activities.

24 Claims, No Drawings

IMMUNE-STIMULATING AND CANCEROSTATIC 1-ACYL-2-CYANOAZIRIDINES

The present invention is concerned with new 1-acyl-2-cyanoaziridines and with the preparation thereof.

It is known from German Democratic Republic Patent Specification No. 110,492 that 1-acyl-2-cyanoaziridines are cytostatically active. For example, after the intravenous administration of 1-carbamoyl-2-cyanoaziridine to rats, a marked increase of the leucocytes and of the lymphocytes was observed, whereas the number of erythrocytes remained almost unchanged; furthermore a marked increase in antibody-forming spleen cells was observed (see Federal Republic of Germany Patent Specification No. 2,528,460). Consequently, this compound can also be used therapeutically in the case of infections brought about by pathogenic micro-organisms and viruses. However, a great disadvantage is the complete ineffectiveness of this compound when administered orally.

Thus, the problem exists of finding cancerostatic and immune-stimulating therapeutic compounds which, while having the same or increased effectiveness and lower toxicity, can also be administered orally.

We have now found a group of new 1-acyl-2-cyanoaziridines which also when administered orally bring about marked leucocytosis with an immune-stimulating action and can, therefore, be used as immune-stimulating therapeutics.

Thus, according to the present invention, there are provided 1-acyl-2-cyanoaziridines of the general formula:

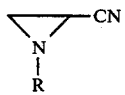

(I)

wherein R is a radical of the general formula

in which $R_1$ is a hydrogen atom or a nitrile, carbamoyl, lower alkoxycarbonyl or acyl radical or a saturated or unsaturated cycloaliphatic hydrocarbon radical which can be substituted one or more times by halogen, nitrile, aryl, aryloxycarbonyl, lower alkoxy or acyloxy or by lower alkoxycarbonyl, optionally substituted by a lower N,N-dialkylamino radical, or by lower alkyl, optionally substituted by a ureido, lower acylamino or acyloxy radical, or by an amino group substituted by carbamoyl, alkoxycarbonyl or acyl, or by a radical of the formula:

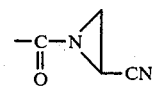

or which can optionally be condensed with a phenyl radical or can contain a hydrocarbon bridge member containing up to 3 carbon atoms or an oxygen bridge member, or $R_1$ is a radical of the formula:

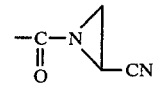

or a straight-chained or branched saturated or unsaturated aliphatic hydrocarbon radical containing 2 to 18 carbon atoms; or $R_1$ is a straight-chained or branched, saturated or unsaturated hydrocarbon chain which is substituted one or more times by nitrile, halogen, nitro, aryl, aryloxy, arylthio, optionally substituted hetarylthio, saturated or unsaturated cycloaliphatic hydrocarbonyl, which can contain a bridge containing up to 3 carbon atoms, optionally N-alkylated carbamoyl, lower alkoxycarbonyl, optionally substituted by an N,N-dialkylamino group, optionally N-alkylated sulphamoyl or optionally N-alkylated carbamic acid group; or by a lower acyl, acyloxy, alkylsulphonyl or alkylsulphinyl group or a lower alkylthio or alkoxy group, optionally substituted by phenyl or by a radical of the formula:

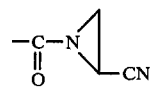

or by an optionally substituted aromatic or non-aromatic heterocyclic radical, or by a radical of the formula:

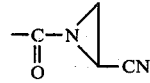

or by a lower dialkoxyphosphoryloxy or dialkoxyphosphonyl radical, or by a radical of the formula:

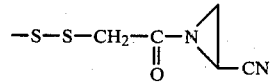

or a radical of the general formula:

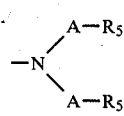

in which the groups $-A-R_5$ can be the same or different, A being a valency bond, a carbonyl, thiocarbonyl or $-CO-CH_2-$ group and $R_5$ being hydrogen, nitrile, aryl, a lower straight-chained or branched, saturated or unsaturated aliphatic hydrocarbon radical, which can optionally be substituted one or more times by halogen, aryl, a radical of the formula:

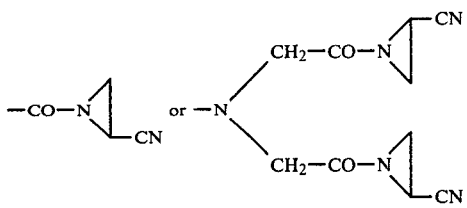

or $R_5$ being a lower alkoxy radical optionally substituted by aryl, or a lower alkylthio, alkylsulphinyl or alkylsulphonyl group, an amino group optionally substituted one or more times by phenyl, heteroaryl, lower alkyl, alkylsulphonyl, acylamidocarbimidoyl or acyl, or an N-methyleneamino radical substituted by an optionally substituted aromatic heterocyclic radical or by an aryl or lower alkyl group, or being an arylthio, arylsulphinyl or arylsulphonyl group or an aryloxy or a cycloalkyl radical or being an optionally substituted aromatic or non-aromatic heterocycle, the aryl radicals in all of the said groups being optionally substituted one or more times by halogen, nitrile, nitro, sulphamoyl, optionally N-alkylated carbamoyl, trifluoromethyl, phenyl, phenoxy, methylenedioxy group, lower alkyl, alkoxy, acyl, acyloxy, alkoxycarbonyl, alkylthio, alkylsulphinyl, alkylsulphonyl, phenylsulphonyl, amino substituted one or more times by alkyl, phenyl or acyl, or by a radical of the formula:

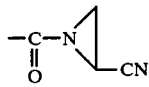

or $R_1$ is an optionally substituted aromatic or nonaromatic heterocyclic radical, or $R_1$ is an aryl radical which is substituted one or more times by halogen, nitrile, trifluoromethyl or sulphamoyl, or by phenyl, phenoxy or phenulsulphonyl radical optionally substituted by halogen, alkyl, alkoxy or a radical of the formula:

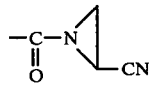

or by a methylenedioxy group, or by a lower alkyl radical optionally substituted by carbamoyl, lower alkoxycarbonyl, alkoxy, acyloxy, N-alkylaminocarbonyloxy, N-alkoxycarbonylamino or N-acylamino, or by a lower alkoxy, acyl, acyloxy, alkylthio, alkoxycarbonyl, alkylsulphinyl or alkylsulphonyl group, or by an amino group substituted by alkyl, aryl, acyl or alkoxycarbonyl or by carbamoyl optionally substituted by alkyl or aryl, or by an optionally N-alkylated carbamoyl group, or by a radical of the formula:

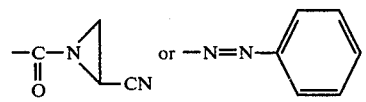

or R is a radical of the general formula $-S(O)_n-R_2$, in which n is 0 or 1 and $R_2$ is a straight-chained or branched, saturated or unsaturated aliphatic hydrocarbon radical which can optionally be substituted one or more times by halogen, or is a cycloalkyl radical or is an aryl radical optionally substituted by phenyl, halogen, nitro, lower alkyl, alkoxy, alkylthio or alkylsulphonyl or is an optionally substituted hetaryl radical; or R is a radical of the general formula $-SO_2-R_2'$, in which $R_2'$ is an optionally N-alkylated amino group, a straight-chained or branched, saturated or unsaturated aliphatic hydrocarbon radical which can be optionally substituted one or more times by halogen or by N-acylamino group or is a cycloalkyl radical or a phenyl radical substituted by alkoxy, phenoxy or phenyl; or is a naphthyl or optionally substituted heteroaryl radical or R is a radical of the general formula:

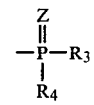

in which Z is an oxygen or sulphur atom and $R_3$ and $R_4$, which can be the same or different, are hydroxyl, piperidino, anilino, N-alkoxycarbonylamino, phenyl, phenoxy, lower alkyl or alkoxy or a radical of the formula:

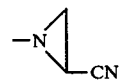

or $R_3$ and $R_4$ together signify a lower alkylenedioxy group; or R is the residue of 3-camphor-carboxylic acid, abietic acid or 6-acetamidopenicillin-carboxylic acid, all the above-mentioned aromatic and non-aromatic heterocyclic radicals being optionally substituted one or moe times by halogen, nitro, phenyl, lower acyl, acyloxy, alkyl, alkoxy, alkylthio, alkylsulphinyl, alkylsulphonyl or amino groups, which amino groups are substituted one or more times by alkyl, aryl or acyl, and wherein the N-containing heterocyclic radicals can also be oxidized; as well as the pharmacologically acceptable salts thereof.

The present invention also includes within its scope all stereoisomeric compounds of general formula (I) which are formed, for example, due to the presence of asymmetrical carbon atoms or due to cis-trans isomerism. The products obtained in the form of mixtures can be separated in the manner known from and described in the literature.

Thus, the 1-acyl-2-cyanoaziridines of general formula (I) according to the present invention are compounds, the acyl radicals of which are derived from carboxylic, sulphonic, sulphinic, sulphenic, phosphonic or phosphoric acids.

Insofar as not stated to the contrary, an aliphatic hydrocarbon radical of the substituents $R_1$, $R_2$, $R_2'$, $R_3$, $R_4$ and $R_5$, alone or in combination, for example in alkoxy, alkoxycarbonyl, acyl, acyloxy, N-alkylamino, N,N-dialkylamino, alkylsulphonyl, alkylsulphinyl, alkylthio, dialkoxyphosphoryloxy or dialkoxyphosphonyl, is to be understood to mean an aliphatic hydrocarbon radical containing up to 6 and preferably up to 4 carbon atoms, which can be straight-chained, branched or cyclic or saturated or unsaturated, the methyl and ethyl radicals being preferred.

A lower acyl radical of the substituents $R_1$, $R_2$, $R_2'$ and $R_5$ means alone or in combination, for example in acyloxy or acylamino, the residue of an organic acid, mention being made, in general, of alkylcarboxylic acids and especially of acids containing up to 6 carbon atoms and of aryl and also of heteroaryl carboxylic acids and of the corresponding sulphonic acids, the acetyl and benzoyl radicals being preferred.

Cycloaliphatic hydrocarbon radicals of the substituents $R_1$, $R_2$, $R_2'$ and $R_5$ are preferably saturated or unsaturated radicals containing 3 to 8 carbon atoms as ring members, examples of saturated rings including cyclopropyl, cyclobutyl, cyclopentyl, cyclohexyl, cycloheptyl and cyclooctyl groups and examples of unsaturated rings including cyclopentenyl, cyclohexenyl, cyclohexadienyl and cycloheptenyl radicals.

Cyclic radicals condensed with phenyl include, for example, the indane and 1,2,3,4-tetrahydronaphthalene radicals. Bridged carbocyclic radicals include, for example, the adamantyl, norbornane and norbornene radicals and a preferred cyclic hydrocarbon radical bridged with oxygen is the 7-oxabicyclo[2.2.1]heptane radical.

The substituted straight-chained or branched, saturated or unsaturated hydrocarbon chains of the substituent $R_1$ can contain up to 18, preferably up to 6 and especially 1 or 2 carbon atoms. Preferred chains containing at least one double bond include the —CH=CH— and —CH=CH—CH=CH— groups and the preferred chains containing at least one triple bond include the —C≡C— group.

According to the present invention, halogen is to be understood to mean fluorine, chlorine, bromine and iodine, fluorine and chlorine being preferred.

Aryl radicals are to be understood to mean aromatic carbocyclic radicals, preferably phenyl, naphthalene, phenanthrene, anthracene, fluorene and indene and especially phenyl.

The non-aromatic heterocyclic radicals of the substituents $R_1$ and $R_5$ are, in general, to be understood to mean heterocyclic 3- to 8-membered ring systems which, apart from carbon atoms, also contain one or more heteroatoms, such as oxygen, sulphur or optionally alkylated or acylated nitrogen, the carbon atoms of which can also be substituted by oxo and/or thioxo residues. Furthermore, the heterocyclic radicals can also contain one or more fused benzene rings.

Preferred non-aromatic heterocyclic radicals include the N-succinimido, N-maleinimido, N-phthalimido, N-imidazolidinone, N-piperidinone, N-pyridone, N-pyrrolidinone, N-piperazinone, N-pyrazolinone, aziridine, pyran, piperidine, morpholine, piperazine, rhodanine and xanthene radicals.

Preferred substituted and non-aromatic heterocyclic radicals include the N-(N'-methyl)-imidazolidinone, 2-cyanoaziridine, N-acetylpyrrolidine and 2,3-dimethyl-1-phenyl-pyrazolidinone (antipyrin) radicals.

Aromatic heterocyclic radicals of the substituents $R_1$, $R_2$, $R_2'$ and $R_5$ can, in general, be 5- or 6-membered ring systems containing one or more heteroatoms, such as oxygen, sulphur or optionally alkylated or acylated nitrogen; the heterocycles can also be condensed with one or two benzene rings or with a further heterocycle and the nitrogen-containing aromatic radicals can also be oxidized on the nitrogen atom.

Preferred aromatic heterocyclic radicals include the pyridine, quinoline, furan, thiophene, benzofuran, pyridazine, pyrazine, pyrazole, s-triazolo[4.3-b]pyridazine, pyrimidine, imidazole, pyrrole, indole, thiazole and purine radicals.

Preferred substituted aromatic heterocyclic radicals include the 1-methyl-3-nitropyrazole, 3-methylthiopyridazine, 3-methylsulphonylpyridazine, 2-methylpyridine, 2-nitrothiazole, 2-acetylaminothiazole, 2-methylthiazole, 1-methylpyrrole, 1-acetylindole, 2,4-dimethyl-1,3-diacetylpyrrole, 1-acetylimidazole and 6-chloropyridazine radicals.

A preferred oxidized aromatic nitrogen-containing heterocycle is a pyridine-N-oxide radical.

The new compounds according to the present invention can be prepared, for example, by reacting 2-cyanoaziridine with a compound of the general formula:

R—X        (II), wherein R has the same meaning as above and X is hydroxyl, halogen, azide of lower alkoxy, alkoxycarbonyloxy or phenoxycarbonyloxy or a radical of the general formula —OR, the substituents R being the same or different, in an inert solvent, optionally in the presence of water- and/or acid-binding condensation agents.

The inert solvent used can be, for example, tetrahydrofuran, methylene chloride, dimethyl formamide, dioxan, diethyl ether, pyridine or water. When a free acid is used as reaction component, the condensation agent is preferably dicyclohexylcarbodiimide or carbonyldiimidazole in molar or somewhat more than molar amount.

The reaction can be carried out at a temperature of from $-10°$ to $+100°$ C.

When acid halides or acid anhydrides are used as reaction components with the 2-cyanoaziridine, it is preferable to add an acid-binding agent, for example triethylamine or some other tertiary organic amine. However, in many cases, there can also be used a mineral base, such as sodium hydroxide or calcium hydroxide, or an alkali metal or alkaline earth metal carbonate, for example potassium carbonate or calcium carbonate.

In the case of reactions in aqueous media, it is preferable also to add a water-immiscible organic solvent, for example benzene, diethyl ether or ethyl acetate.

Some of the compounds of general formula (II) used as reaction components are new and can be prepared by known processes.

The new compounds according to the present invention can also be prepared by cyclizing compounds of the general formula:

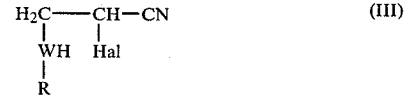

$$\begin{array}{c} H_2C\text{———}CH\text{—}CN \\ | \quad\quad\quad | \\ NH \quad\quad Hal \\ | \\ R \end{array} \quad (III)$$

wherein R has the same meaning as above and Hal is a halogen atom, in the presence of an acid-binding agent.

Some of the compounds of general formula (III) are new and can be prepared by reacting the corresponding acid amides of the general formula $R.NH_2$, wherein R has the same meaning as above, with α-haloacrylonitriles or with 2,3-dihalopropionitriles.

In some cases, for example when R is a sulphonic acid residue, it is possible to obtain the compounds (I) according to the present invention directly by reaction of the amide with an α-haloacrylonitrile, without isolation of the intermediate products (III), it being preferable to carry out the reaction in an inert solvent at a temperature below 5° C. in the presence of an alkali.

Furthermore, it is possible to convert compounds of general formula (I) into other compounds of general formula (I). Thus, for example, substituted mercapto groups can be oxidized with appropriate oxidation agents to give the corresponding sulphines and sulphones and amines with free hydrogen atoms and aromatic and non-aromatic carbocycles and heterocycles can be substituted or possibly oxidized.

Furthermore, compounds of general formula (I), when they contain appropriate acidic or basic groups, can be converted into pharmacologically accpetable salts by reaction with inorganic or organic bases or acids.

When administered orally or intravenously, the new compounds of general formula (I) according to the present invention bring about a marked increase of the leukocytes and lymphocytes with almost unchanged erythrocyte count and possess strong immune-stimulating and cancerostatic properties. Furthermore, they stimulate the bone marrow, bringing about an increased formation of cells of the erythropoetic series and release of these cells into the peripheral blood circulation. Therefore, the new compounds according to the present invention can be used as active materials in pharmaceutical compositions for the treatment of bacterial and viral infections, as well as cancerostatics.

For the preparation of pharmaceutical compositions with immune-stimulating and cancerostatic action, at least one compound of general formula (I) is mixed in known manner with an appropriate solid or liquid pharmaceutical diluent or carrier and formed, for example, into tablets or dragees and, with the addition of appropriate adjuvants, suspended or dissolved in water or in an oil, such as olive oil, and placed into hard gelatine capsules.

The oral forms of administration are preferably provided with a coating which first dissolves in the alkaline medium of the small intestine or are admixed with an appropriate carrier material, for example a higher fatty acid or carboxymethyl-cellulose. Solid materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols); compositions suitable for oral administration can, if desired, contain flavoring and/or sweetening agents.

As injection medium, it is preferred to use water which contains the additives usual for injection solutions, such as stabilizing agents, solubilizing agents, buffers and materials for regulating the osmotic pressure. Additives of this type include, for example, phosphate and carbonate buffers, ethanol, complex-forming agents (such as ethylenediamine-tetraacetic acid and the non-toxic salts thereof), high molecular weight polymers (such as liquid polyethylene oxide) for viscosity regulation and sodium chloride, mannitol and the like for regulating the osmotic pressure.

Apart from the compounds mentioned in the following examples, preferred compounds according to the present invention include the following:
1-formyl-2-cyanoaziridine
1-formylcarbonyl-2-cyanoaziridine
1-acetylcarbonyl-2-cyanoaziridine
1-methoxyacetyl-2-cyanoaziridine
1-(2-pyridylacetyl)-2-cyanoaziridine
1-(2-naphthyloxyacetyl)-2-cyanoaziridine
1-(n-butylsulphonylacetyl)-2-cyanoaziridine
1-(1-piperidin-2-on)-acetyl)-2-cyanoaziridine
1-(n-butylsulphonylacetylglycyl)-2-cyanoaziridine
1-(4-phenylbenzamidoacetyl)-2-cyanoaziridine
1-(N-maleinimidoacetyl)-2-cyanoaziridine
1-(N-phenylsulphenylaminoacetyl)-2-cyanoaziridine
1-(p-tolylsulphinylamidoacetyl)-2-cyanoaziridine
1-(isonicotinoylamidoacetyl)-2-cyanoaziridine
1-(3-acetylhydrazinoacetyl)-2-cyanoaziridine
1-(N-succinimidoaminoacetyl)-2-cyanoaziridine
1-benzylidenchydrazinoacetyl-2-cyanoaziridine
1-(2-furfurylidenehydrazinoacetyl)-2-cyanoaziridine
1-(2-acetoxybenzamidoacetyl)-2-cyanoaziridine
1-(4-carbamoylbenzoyl)-2-cyanoaziridine
1-(3-methylsulphonylpyridazine-6-carbonyl)-2-cyanoaziridine
1-isoicotinoyl-2-cyanoaziridine
1-(triazolo[4,3-b]pyridazine-6-carbonyl)-2-cyanoaziridine
1-(4-methoxybenzenesulphonyl)-2-cyanoaziridine
1-ethylenedioxyphosphoryl-2-cyanoaziridine
1-acetylenecarbonyl-2-cyanoaziridine
1-dimethylaminocarbonylacetyl-2-cyanoaziridine
1-dimethoxyphosphonoacetyl-2-cyanoaziridine
1-dimethylsulphamoylacetyl-2-cyanoaziridine
1-cyanoacetyl-2-cyanoaziridine
oxalyl-bis-1-(2-cyanoaziridine)
acetylenedicarbonyl-bis-1-(2-cyanoaziridine)
1-(2-naphthoyl)-2-cyanoaziridine
1-(2-nitrothiazole-5-carbonyl)-2-cyanoaziridine
1-(2-acetamido-4-methylthiazol-5-carbonyl)-2-cyanoaziridine
N,N-dimethylglycyl-2-cyanoaziridine
1-(5-mesylhydantoyl)-2-cyanoaziridine
1-(5,5-dimethylhydantoyl)-2-cyanoaziridine
1-(N-imidazolacetyl)-2-cyanoaziridine
1-(N-pyrazolacetyl)-2-cyanoaziridine
1-(N-methylimidazolidin-2-on-N'-acetyl)-2-cyanoaziridine
1-[(6-methylpyridine-2-carbonyl)-glycyl]-2-cyanoaziridine
1-[(2-methylthiazole-5-carbonyl)-glycyl]-2-cyanoaziridine
1-(n-butylsulphinylacetylglycyl)-2-cyanoaziridine
1-(N-acetyliminodiacetyl)-bis-1-(2-cyanoaziridine)
1,2-ethylenediaminotetra-(1-acetyl-2-cyanoaziridine)
1-sulphamoyl-2-cyanoaziridine
1-dimethylsulphamoyl-2-cyanoaziridine
1-(2-cyclohexenyldodecanecarbonyl)-2-cyanoaziridine
1-(xanthene-9-carbonyl)-2-cyanoaziridine
1-(1,2,3,4-tetrahydronaphthalene-2-carbonyl)-2-cyanoaziridine
1-(pyridine-2-carbonyl)-2-cyanoaziridine-N-oxide
1-abietinoyl-2-cyanoaziridine
1-(4-biphenylsulphonyl)-2-cyanoaziridine
1-[3-(5-norbornen-2-yl)-acryloyl]-2-cyanoaziridine
1-(3-nitropropionyl)-2-cyanoaziridine
1-(N-methylpyrrole-2-carbonyl)-2-cyanoaziridine
1-(1-methyl-1-cyclohexanecarbonyl)-2-cyanoaziridine
1-(N-acetyl-3-indolylacetyl)-2-cyanoaziridine
1-(1,3-diacetyl-2,4-dimethylpyrrole-5-carbonyl)-2-cyanoaziridine
1-(1-adamantanecarbonyl)-2-cyanoaziridine
1-(p-ethoxyphenylacetyl)-2-cyanoaziridine
1-(p-acetamidobenzoylglycyl)-2-cyanoaziridine
1-acetamidomethanesulphonyl-2-cyanoaziridine 1-(6-acetamidopenicillan-carbonyl)-2-cyanoaziridine
1-(9-anthracenecarbonyl)-2-cyanoaziridine
1-(azobenzene-4-carbonyl)-2-cyanoaziridine
1-p-chlorophenoxyacetyl-2-cyanoaziridine
1-p-chlorophenylcyclobutane-1-carbonyl-2-cyanoaziridine
cyclobutane-1,2-dicarbonyl-bis-1-(2-cyanoaziridine)
1-cycloheptanecarbonyl-2-cyanoaziridine
1-[(cyclopent-2-ene)-acetyl]-2-cyanoaziridine
1-(3,4-dihydro-2H-pyran-2-carbonyl)-2-cyanoaziridine
O,O'-dibenzoyltartaroyl-bis-1-(2-cyanoaziridine)
4,4'-(2-cyanoaziridine-1-carbonyl)-diphenylsulphone
1-(9-fluorenecarbonyl)-2-cyanoaziridine
1-(ethoxy-hydroxyphosphoryl)-2-cyanoaziridine
1-(diphenoxyphosphoryl)-2-cyanoaziridine
piperidinophosphoryl-bis-1-(2-cyanoaziridine)
ethoxycarbonylaminophosphoryl-bis-1-(2-cyanoaziridine)
Phenylaminophosphoryl-bis-1-(2-cyanoaziridine)
1-(dipiperidino-phosphoryl)-2-cyanoaziridine
1-(methane-hydroxyphosphonyl)-2-cyanoaziridine
1-(benzene-hydroxyphosphonyl)-2-cyanoaziridine
1-(methane-methoxyphosphonyl)-2-cyanoaziridine
1-(3-dimethylaminoethoxycarbonylpropionyl)-2-cyanoaziridine
1-(2-benzoyloxypropionyl)-2-cyanoaziridine
1-(2-α-furoyloxypropionyl)-2-cyanoaziridine
1-(O-methylaminocarbonyolmandeloyl)-2-cyanoaziridine
1-(O-dimethoxyphosphorylmandeloyl)-2-cyanoaziridine
1-[3-(N-allylcarbamoyl)-amidopropionyl]-2-cyanoaziridine
1-[5-(pyrimid-2-ine)-hydantoyl]-2-cyanoaziridine
1-[(N-phenylthiocarbamoyl)-glycyl]-2-cyanoaziridine
1-(2,2-dichlorocyclopropanecarbonyl)-2-cyanoaziridine
1-(1-ethoxycarbonylcyclobutanecarbonyl)-2-cyanoaziridine
1-(1-dimethylaminoethoxycarbonylcyclobutanecarbonyl)-2-cyanoaziridine
1-(1-ureidomethylcyclopropanecarbonyl)-2-cyanoaziridine
1-(1-ethoxycarbonylamidocyclopentanecarbonyl)-2-cyanoaziridine
1-(1-acetamidocyclopentanecarbonyl)-2-cyanoaziridine
1-p-diethylaminocarbonylbenzoyl-2-cyanoaziridine
1-p-α-furoylbenzoyl-2-cyanoaziridine
1-p-ureidobenzoyl-2-cyanoaziridine
1-p-acetoxymethylbenzoyl-2-cyanoaziridine
1-p-formamidomethylbenzoyl-2-cyanoaziridine
1-p-isobutoxycarbonylamidomethylbenzoyl-2-cyanoaziridine
1-p-methoxycarbonylethylbenzoyl-2-cyanoaziridine
1-p-carbamoylethylbenzoyl-2-cyanoaziridine
1-(N,O-diacetyltyrosyl)-2-cyanoaziridine
1-(N,N'-diacetyllysyl)-2-cyanoaziridine
1-(N,N'-diacetylhistidyl)-2-cyanoaziridine
1-(N,N'-diacetylarginyl)-2-cyanoaziridine
1-(N,N'-diacetyltryptophyl)-2-cyanoaziridine
1-(N,O-diacetylseryl)-2-cyanoaziridine
1-(7-oxabicyclo[2.2.1]heptane-2-carbonyl)-2-cyanoaziridine
1-(2-naphthalenesulphonyl)-2-cyanoaziridine.

The following examples are given for the purpose of illustrating the present invention:

EXAMPLE 1

1-p-Methoxybenzoyl-2-cyanoaziridine.

1.52 g. p-Methoxybenzoic acid is dissolved in 20 ml. dioxan and mixed at 10° C. with a solution of 0.68 g. 2-cyanoaziridine in 3 ml. dioxan. A solution of 2.06 g. dicyclohexylcarbodiimide in 4 ml. dioxan is added thereto and the reaction mixture is stirred for 2 hours at 8°-10° C. The crystals formed (2 g. 1,3-dicyclohexylurea; m.p. 225°-230° C.) are filtered off with suction and the filtrate is evaporated in a vacuum. The semi-solid evaporation residue (3.88 g.) is triturated with 3 ml. anhydrous diethyl ether, the crystals obtained (0.6 g.) are filtered off with suction, the filtrate is evaporated in a vacuum and the evaporation residue (2.45 g.) is again triturated with 3-4 ml. diethyl ether and filtered with suction to give 0.59 g. 1-p-methoxybenzoyl-2-cyanoaziridine; m.p. 81°-83° C. A further 0.18 g. of the desired product are obtained from the mother liquor by again evaporating and triturating the evaporation residue with diethyl ether.

EXAMPLE 2

1-(2-Methylthiobenzoyl)-2-cyanoaziridine.

1.86 g. 2-Methylthiobenzoyl chloride is dissolved in 14 ml. anhydrous diethyl ether and this solution is added dropwise at ambient temperature to a solution of 0.68 g. 2-cyanoaziridine in 8.6 ml. aqueous 2 N sodium carbonate solution and then stirred for 2 hours, whereafter the ethereal phase is separated off and evaporated to give 1.72 g. of residue which is triturated with 4 ml. isopropanol. There is thus obtained 1.35 g. 1-(2-methylthiobenzoyl)-2-cyanoaziridine; m.p. 67°-69° C.

EXAMPLE 3

1-(Pyridine-2-carbonyl)-2-cyanoaziridine 2.96 g. Pyridine-2-carboxylic acid are heated under reflux for 10 minutes with 54 ml. thionyl chloride, excess thionyl chloride is then evaporated off under vacuum, the evaporation residue is taken up in anhydrous diethyl ether, 1.2 g. of undissolved material is filtered off, the clear ethereal filtrate, which contains crude pyridine-2-carboxylic acid chloride, is introduced into a solution of 0.84 g. 2-cyanoaziridine and 1.45 g. triethylamine in 60 ml. anhydrous diethyl ether, the reaction mixture is stirred for 1 hour at ambient temperature, the resultant hydrochloride (1.9 g.) is filtered off with suction and the ethereal filtrate is evaporated. The evaporation residue (2.1 g.) is triturated twice with 3 ml. amounts of diethyl ether and the resulting crystals are filtered off with suction to give 0.76 g. 1-(pyridine-2-carbonyl)-2-cyanoaziridine; m.p. 124°-127° C. This product is contaminated with a small amount of a substance which is monochlorinated in the pyridine nucleus.

EXAMPLE 4

1-(2-Furoyl)-2-cyanoaziridine.

A solution of 1.3 g. furoyl chloride in 5 ml. anhydrous diethyl ether is added, with ice cooling, to a solution of 0.7 g. 2-cyanoaziridine and 1.22 g. triethylamine in 10 ml. anhydrous diethyl ether, stirred for 1 hour and the precipitated hydrochloride is filtered off with suction. The ethereal mother liquor is evaporated and the evaporation residue is triturated with 2 ml. diethyl ether to give 0.99 g. of product with a melting point of 73°-76°

C. which, after again triturating with 2 ml. diethyl ether, gives 0.75 g. 1-(2-furoyl)-2-cyanoaziridine; m.p. 77°–78° C.

EXAMPLE 5

1-Acryloyl-2-cyanoaziridine 1.6 ml. Acryloyl chloride in 10 ml. diethyl ether is added dropwise to a solution of 1.4 g. 2-cyanoaziridine and 2.42 g. triethylamine in 30 ml. anhydrous diethyl ether. The reaction mixture is stirred for 1 hour, the precipitated hydrochloride is filtered off with suction and the ethereal mother liquor is evaporated to give 2.26 g. of a yellow oil. This is fractionated on an approximately 25 cm. long silica gel column (containing 50 g. silica gel) using chloroform as elution agent, the fractions which first run out and which are thin layer chromatographically uniform (silica gel plate, chloroform as elution agent) are combined (with the substance spot next to the front) and evaporated to give 1.07 g. of the desired 1-acryloyl-2-cyanoaziridine in the form of a colorless oil.

Analysis:
$C_6H_6N_2O$ (M.W. 122)

| | | | |
|---|---|---|---|
| calc.: | C 59.02%; | H 4.92%; | B 22.95% |
| found: | 58.32%; | 4.98%; | 22.54% |

The mass and NMR spectra confirm the structure.

EXAMPLE 6

1-(3-Carbethoxyacryloyl)-2-cyanoaziridine

A solution of 2.87 g. trans-3-ethoxycarbonylacryloyl chloride (b.p. 85° C./13 mm.Hg) in 20 ml. diethyl ether is slowly added dropwise at 0° C. to a solution of 1.2 g. 2-cyanoaziridine and 2.2 g. triethylamine in 60 ml. anhydrous diethyl ether. The reaction mixture is then stirred for 1 hour at 0° C. and then for a further 2 hours at ambient temperature, the precipitated hydrochloride is filtered off with suction and the diethyl ether is evaporated off, 2.28 g. of solid evaporation residue remaining behind. This is triturated twice with 3 ml. amounts of diethyl ether to give 1 g. 1-(3-carbethoxyacryloyl)-2-cyanoaziridine; m.p. 54°–56° C.

EXAMPLE 7

1-n-Butylthioacetyl-2-cyanoaziridine 1.03 g. Dicyclohexylcarbodiimide in 5 ml. diethyl ether is added at 0° C. to a solution of 0.74 g. n-butylthioacetic acid and 0.34 g. 2-cyanoaziridine in 15 ml. diethyl ether. The reaction mixture is stirred for 1 hour at 0° C. and for 2 hours at ambient temperature, the precipitated dicyclohexylurea (1.08 g.) is filtered off with suction, the ethereal filtrate is shaken twice with 5 ml. amounts of water and the ethereal phase is then dried and evaporated. There is thus obtained 0.8 g. 1-n-butylthioacetyl-2-cyanoaziridine in the form of a viscous oil.

The same compound is also obtained when a solution of 0.99 g. n-butylthioacetyl chloride in 10 ml. anhydrous diethyl ether is added dropwise to a solution of 0.73 g. triethylamine and 0.42 g. 2-cyanoaziridine in 20 ml. diethyl ether, the reaction mixture is stirred for 1 hour, the precipitated hydrochloride is filtered off with suction and the ethereal solution is evaporated and again shake out with water. After drying, the diethyl ether is evaporated off to give 0.87 g. 1-n-butylthioacetyl-2-cyanoaziridine in the form of a viscous oil.

Analysis:
$C_9H_{14}N_2OS$ (M.W. 198)

| | | | |
|---|---|---|---|
| calc.: | C 54.55%; | H 7.07%; | N 14.14% |
| found: | 54.31%; | 7.07%; | 14.00% |

EXAMPLE 8

1-(N-p-chlorobenzoylaminoacetyl)-2-cyanoaziridine 4.27 g. N-p-chlorobenzoylglycine (m.p. 147°–148° C.) are dissolved in 36 ml. pure tetrahydrofuran, 1.36 g. 2-cyanoaziridine is added thereto and, after cooling to 0° C., 4.3 g. dicyclohexylcarbodiimide are added. The reaction mixture is stirred for 2 hours at 0° C., the precipitated dicyclohexylurea is filtered off with suction, the filtrate is evaporated in a vacuum and the evaporation residue is dissolved in ethyl acetate, whereafter sufficient petroleum ether is added to precipitate out a greasy material. The solvent is now separated off from this greasy material and this greasy material repeatedly triturated with resh petroleum ether and then left to stand overnight with petroleum ether. After filtration, there are obtained 2.1 g. 1-(N-p-chlorobenzoylaminoacetyl)-2-cyanoaziridine (m.p. 65°–68° C.), which is still contaminated with a little dicyclohexylurea.

EXAMPLE 9

1-(4-Benzamidobutyryl)-2-cyanoaziridine 2.07 g. 4-Benzoylaminobutyric acid (m.p. 85°–86° C.) are dissolved in 13 ml. dioxan, a solution of 0.68 g. 2-cyanoaziridine in 2 ml. dioxan is added thereto and a solution of 2.06 g. dicyclohexylcarbodiimide in 10 ml. dioxan is then added dropwise at 10°–15° C., whereafter the solution is stirred for 30 minutes at 10°–15° C. and subsequently for 3 hours at ambient temperature and left to stand overnight. The precipitated dicyclohexylurea (2.48 g.) is filtered off with suction, washed with dioxan and the filtrate is evaporated in a vacuum. The oily evaporation residue obtained is triturated with diethyl ether to give 1.8 g. 1-(4-benzamidobutyryl)-2-cyanoaziridine (m.p. 114°–116° C.), which is contaminated with a little dicyclohexylurea.

EXAMPLE 10

1-(1-β-Naphthoylamidoacetyl)-2-cyanoaziridine 2.29 g. β-Naphthoylglycine in 18 ml. tetrahydrofuran and 0.68 g. 2-cyanoaziridine are, as a suspension, mixed portionwise at 0° C. with 2.15 g. dicyclohexylcarbodiimide. The reaction mixture is stirred for 2 hours at 0° C. and the precipitated dicyclohexylurea (2.18 g., m.p. 228° C.) is filtered off with suction, washed with tetrahydrofuran and diethyl ether into the filtrate and the filtrate is then evaporated in a vacuum to give an oil which is triturated three times with diethyl ether to give 1.3 g. 1-(β-naphthoylamidoacetyl)-2-cyanoaziridine; m.p. 116°–118° C.

EXAMPLE 11

1-Phenylacetamidoacetyl-2-cyanoaziridine

In a manner analogous to that described in Example 10, using 2.15 g. dicyclohexylcarbodiimide, 1.93 g. phenylacetylglycine (m.p. 144°–146° C.) and 0.68 g.

2-cyanoaziridine, there is obtained 1.7 g. 1-phenylacetamidoacetyl-2-cyanoaziridine; m.p. 114°–116° C.

EXAMPLE 12

1-(Cyclohexylcarbonamidoacetyl)-2-cyanoaziridine

In a manner analogous to that described in Example 10, using 1.85 g. cyclohexanecarbonylglycine (m.p. 150°–152° C.), 0.68 g. 2-cyanoaziridine and 2.15 g. dicyclohexylcarbodiimide, there is obtained, after stirring the reaction mixture for 3 hours at 0° C., 0.95 g. 1-(cyclohexylcarbonamidoacetyl)-2-cyanoaziridine; m.p. 101°–102° C.

EXAMPLE 13

1-Cyclohexylacetamidoacetyl-2-cyanoaziridine

In a manner analogous to that described in Example 10, from 1.98 g. crude cyclohexylacetamidoacetic acid (m.p. 52° C.), 0.68 g. 2-cyanoaziridine and 2.15 g. dicyclohexylcarbodiimide, there is obtained after stirring for 3 hours at 0° C., 1 g. 1-cyclohexylacetamidoacetyl-2-cyanoaziridine (m.p. 133°–135° C.) which, for further purification, is dissolved in 100 ml. ethyl acetate at a temperature of 50° C., some insoluble material is filtered off and the clear filtrate is evaporated in a vacuum at ambient temperature. After triturating the solid evaporation residue with diethyl ether, there is obtained 0.8 g. of the desired compound; m.p. 135°–136° C.

The cyclohexylacetamidoacetic acid used as starting material is prepared as follows: in the course of about 10 minutes, 3.21 g. cyclohexylacetyl chloride (b.p. 83°–85° C./12 mm.Hg) are introduced at 10° C. into a mixture of 2.5 g. glycine in 20 ml. water and 0.8 g. sodium hydroxide, as well as 2 g. anhydrous sodium carbonate. The reaction mixture is stirred for 2.5 hours at 15° C. and repeatedly extracted with diethyl ether. The aqueous phase is acidified, while cooling with ice, with about 8 ml. concentrated hydrochloric acid and an initially oily precipitate is thus obtained which gradually solidifies. It is filtered off with suction, washed with ice water and cold diethyl ether to give 1.98 g. cyclohexylacetylglycine.

EXAMPLE 14

1-Phenoxyacetamidoacetyl-2-cyanoaziridine

In a manner analogous to that described in Example 10, from 2.09 g. phenoxyacetylglycine (m.p. 121°–123° C.), 0.68 g. 2-cyanoaziridine and 2.15 g. dicyclohexylcarbodiimide, there is obtained, after stirring for 3 hours at 0° C., 1.3 g. 1-phenoxyacetamidoacetyl-2-cyanoaziridine; m.p. 72°–74° C.

The phenoxyacetylglycine used as starting material is prepared in a manner analogous to that described in Example 13: from 2.5 g. glycine and 3.41 g. phenoxyacetyl chloride there are obtained 3.4 g. phenoxyacetylglycine.

EXAMPLE 15

1-(2,4-Dichlorobenzamidoacetyl)-2-cyanoaziridine

In a manner analogous to that described in Example 10, from 2.48 g. 2,4-dichlorobenzoylglycine (m.p. 168°–174° C.), 0.68 g. 2-cyanoaziridine and 2.15 g. dicyclohexylcarbodiimide, there is obtained 1.4 g. 1-(2,4-dichlorobenzamidoacetyl)-2-cyanoaziridine in the form of a viscous oil.

| Analysis: | | | |
|---|---|---|---|
| $C_{12}H_9Cl_2N_3O_2$ (M.W. 298) | | | |
| calc.: | C 48.3%; | H 3.02%; | N 14.10% |
| found: | 48.82%; | 3.37%; | 13.6% |

The mass and NMR spectra confirm the structure of the product.

EXAMPLE 16

1-(2-Benzofuroylamidoacetyl)-2-cyanoaziridine

In a manner analogous to that described in Example 10, from 2.19 g. 2-benzofuroylglycine (m.p. 189°–190° C.), 0.68 g. 2-cyanoaziridine and 2.15 g. dicyclohexylcarbodiimide, there are obtained, after stirring for 3 hours at 0° C., 2.07 g. 1-(2-benzofuroylamidoacetyl)-2-cyanoaziridine in the form of a solid material; m.p. 133°–134° C.

The 2-benzofuroylglycine used as starting material is obtained in a yield of 4 g. from 2.5 g. glycine and 3.61 g. coumarilic acid chloride in a manner analogous to that described in Example 13 for the preparation of the starting material used therein.

EXAMPLE 17

1-(Thiophene-2-carbonylamidoacetyl)-2-cyanoaziridine

In a manner analogous to Example 10, from 1.85 g. thiophene-2-carbonylglycine (m.p. 170°–171° C.), 0.68 g. 2-cyanoaziridine and 2.15 g. dicyclohexylcarbodiimide, there are obtained, after stirring the reaction mixture for 3 hours at 0° C., 2 g. 1-(thiophene-2-carbonylamidoacetyl)-2-cyanoaziridine in the form of a viscous oil which still contains a little dicyclohexylurea. The combustion analysis (C, H, N, S) and the mass and NMR spectra confirm the structure of the product.

EXAMPLE 18

1-(N-Succinimidoacetyl)-2-cyanoaziridine

In a manner analogous to Example 10, from 1.57 g. N-succinimidoacetic acid (m.p. 111°–113° C.), 0.68 g. 2-cyanoaziridine and 2.15 g. dicyclohexylcarbodiimide, there is obtained 1.4 g. 1-(N-succinimidoacetyl)-2-cyanoaziridine (m.p. 146°–150° C.). The product, freed from dicyclohexylurea, is purified by treatment with an aqueous solution of sodium bicarbonate.

EXAMPLE 19

1-p-Methylphenylsulphinyl-2-cyanoaziridine

A solution of 5.23 g. crude p-toluenesulphinic acid chloride in 10 ml. anhydrous diethyl ether is added, with cooling, to a solution of 2.1 g. 2-cyanoaziridine and 3.86 g. triethylamine in 50 ml. diethyl ether. The reaction mixture is further stirred for 1 hour, the precipitated hydrochloride is filtered off with suction and the ethereal solution is evaporated, 5.66 g. of residue remaining behind. The evaporation residue is dissolved in a little diethyl ether and shaken out twice with about 5 ml. amounts of water. The ethereal phase is evaporated and the evaporation residue thus obtained (4.58 g.) is triturated with a little diethyl ether, while cooling with ice. Undissolved crystals are filtered off with suction to give 1.05 g. 1-p-methylphenylsulphinyl-2-cyanoaziridine; m.p. 102°–104° C. Further amounts of the desired product are obtained from the trituration mother liquors.

EXAMPLE 20

1-Methylsulphonyl-2-cyanoaziridine

A solution of 1.6 ml. methanesulphonyl chloride in 10 ml. anhydrous diethyl ether is slowly added, with cooling, to a solution of 1.4 g. 2-cyanoaziridine and 2.42 g. triethylamine in 30 ml. diethyl ether. The reaction mixture is further stirred for 1 hour, the precipitated hydrochloride is filtered off with suction and the ethereal filtrate is evaporated. The evaporation residue thus obtained (2.7 g.) is purified by means of column chromatography (150 g. silica gel, 35 cm. layer height; chloroform used as elution agent). In the thin layer chromatogram (silica gel plate) with chloroform as elution agent, two spots are observed, one a short distance from the start and the other one close to the front. Those fractions with the substance near the start are collected, combined and evaporated in a vacuum to give 1 g. 1-methylsulphonyl-2-cyanoaziridine in the form of an oil.

Analysis:
$C_4H_6N_2O_2S$ (M.W. 146)

| | | | |
|---|---|---|---|
| calc.: | C 32.88%; | H 4.11%; | S 21.92% |
| found: | 32.82%; | 4.07%; | 21.70% |

The mass and NMR spectra confirm the structure of the product.

EXAMPLE 21

1-[3-(3-Chloropropionamido)-propionyl]-2-cyanoaziridine

In a manner analogous to Example 10, from 0.9 g. 3-($\beta$-chloropropionylamino)-propionic acid, 0.34 g. 2-cyanoaziridine and 1.1 g. dicyclohexylcarbodiimide, there is obtained, after stirring for 3 hours at 10°–15° C., 0.93 g. 1-[3-(3-chloropropionamido)-propionyl]-2-cyanoaziridine (m.p. 60°–72° C.), which is still contaminated with a little dicyclohexylurea.

The 3-($\beta$-chloropropionamido)-propionic acid used as starting material is obtained from 2.94 g. 3-aminopropionic acid and 2.54 g. 3-chloropropionyl chloride in a manner analogous to that described in Example 13 for the preparation of the starting material. The yield is 1.2 g. (m.p. 110°–112° C.). Since, after acidification with concentrated hydrochloric acid, the desired product does not precipitate out, the aqueous phase is, in this case, repeatedly extracted with ethyl acetate, the combined ethyl acetate extracts are concentrated in a vacuum to a volume of about 200 ml., then neutralized by shaking with solid sodium bicarbonate and finally the clear ethyl acetate solution is evaporated in a vacuum.

EXAMPLE 22

1-Diphenylacetyl-2-cyanoaziridine

A solution of 0.34 g. 2-cyanoaziridine in 1 ml. diethyl ether is added at 0° C. to a solution of 1.06 g. diphenylacetic acid in 10 ml. diethyl ether and the reaction mixture then mixed with 1.03 g. dicyclohexylcarbodiimide dissolved in 4 ml. diethyl ether. The reaction mixture is stirred for 1 hour at 0° C. and then for 2 hours at ambient temperature. 1.06 g. of precipitated dicyclohexylurea (m.p. 226° C.) is filtered off with suction and the ethereal filtrate is concentrated, shaken twice with 4 ml. amounts of water and the ethereal phase is separated off and evaporated to give 0.97 g. 1-diphenylacetyl-2-cyanoaziridine in the form of a yellowish viscous oil. The elementary analysis, as well as the mass and NMR spectra, confirm the structure of the product.

The same compound is also obtained when a solution of 1.15 g. diphenylacetyl chloride in 5 ml. anhydrous diethyl ether is added dropwise at 0° C. to a solution of 0.35 g. 2-cyanoaziridine and 0.6 g. triethylamine in 15 ml. diethyl ether and the reaction mixture then stirred for 1 hour at 0° C. and for 2 hours at ambient temperature. The precipitated hydrochloride is filtered off with suction (0.7 g.) and the ethereal filtrate is concentrated to a volume of about 10 ml. and shaken out twice with 5 ml. amounts of water. After evaporation of the ethereal phase, there is obtained 1.13 g. of the desired compound.

EXAMPLE 23

1-Methoxymalonyl-2-cyanoaziridine 5.9 g. Monomethyl malonate, 3.4 g. 2-cyanoaziridine and 10.8 g. dicyclohexylcarbodiimide are dissolved, with cooling, in 50 ml. tetrahydrofuran. After subsequently stirring for 45 minutes, the dicyclohexylurea which has crystallized out is filtered off and the filtrate is evaporated. There are thus obtained 2.8 g. of crude product which is recrystallized from boiling diethyl ether to give 1-methoxymalonyl-2-cyanoaziridine, which melts at 48°–50° C.

EXAMPLE 24

1-(DL-1-Ethoxy-2-ethylmalonyl)-2-cyanoaziridine 4.3 g. Dicyclohexylcarbodiimide are added, with ice cooling, to 3.2 g. monoethyl DL-ethyl-malonate and 1.36 g. 2-cyanoaziridine in 32 ml. diethyl ether. After 2 days at ambient temperature, the dicyclohexylurea is separated off and the filtrate is evaporated to give an oily evaporation residue which is purified on a silica gel column using heptane-methyl ethyl ketone as solvent. There are thus obtained 2.2 g. 1-(DL-1-ethoxy-2-ethylmalonyl)-2-cyanoaziridine in the form of a colorless oil which is thin layer chromatographically uniform.

EXAMPLE 25

1-Methoxysuccinyl-2-cyanoaziridine 2.64 g. Monomethyl succinate, 1.36 g. 2-cyanoaziridine and 4.3 g. dicyclohexylcarbodiimide in 25 ml. diethyl ether are reacted in the manner described in Example 24 and the reaction mixture is worked up to give 1.75 g. 1-methoxysuccinyl-2-cyanoaziridine in the form of a colorless oil. The product is purified by column chromatography using, as elution agent, chloroform-acetone-cyclohexane (5:5:1 v/v/v).

EXAMPLE 26

1-(DL-O-Acetyllactoyl)-2-cyanoaziridine 2.64 g. DL-O-Acetyllactic acid are dissolved in 26 ml. diethyl ether. 1.36 g. 2-Cyanoaziridine and 4.3 g. dicyclohexylcarbodiimide are added thereto, with ice cooling, and the reaction mixture then stirred for 2 hours. After working up and purifying as described in Example 25, there are obtained 2.2 g. 1-(DL-O-acetyllactoyl)-2-cyanoaziridine in the form of a yellowish oil.

EXAMPLE 27

1-Succinamoyl-2-cyanoaziridine 1.85 g. Succinic acid semiamide are suspended in 35 ml. tetrahydrofuran. 3.4 g. Dicyclohexylcarbodiimide and 1 g. 2-cyanoaziridine are then added thereto, with ice cooling. The reaction mixture is left to stand overnight, whereafter the dicyclohexylurea is filtered off and the filtrate is evaporated to give 0.35 g. 1-succinamoyl-2-cyanoaziridine; m.p. 68°-72° C.

EXAMPLE 28

1-(2-Acetoxy-4-acetaminobenzoyl)-2-cyanoaziridine 4.5 g. N,O-Diacetyl-p-aminosalicylic acid, 1.3 g. 2-cyanoaziridine and 4.1 g. dicyclohexylcarbodiimide are reacted in 45 ml. tetrahydrofuran. After separating off dicyclohexylurea and evaporating, the evaporation residue is crystallized with diethyl ether to give 1.4 g. 1-(2-acetoxy-4-acetaminobenzoyl)-2-cyanoaziridine; m.p. 118°-120° C.

EXAMPLE 29

1-(6-Chloropyridazine-3-carbonyl)-2-cyanoaziridine 1.1 g. 6-Chloropyridazine-3-carboxylic acid are suspended in 11 ml. tetrahydrofuran and 0.47 g. 2-cyanoaziridine and 1.5 g. dicyclohexylcarbodiimide are added thereto, with ice cooling. After subsequently stirring for 1 hour at ambient temperature, the dicyclohexylurea is filtered off, the filtrate is evaporated and the residue is crystallized with diethyl ether to give 0.7 g. 1-(6-chloropyridazine-3-carbonyl)-2-cyanoaziridine; m.p. 109°-115° C.

EXAMPLE 30

1-(N-Acetylglycyl)-2-cyanoaziridine 5.85 g. N-Acetylglycine, 3.4 g. 2-cyanoaziridine and 10.8 g. dicyclohexylcarbodiimide are stirred in 60 ml. tetrahydrofuran for 2 hours at ambient temperature. The precipitated dicyclohexylurea is filtered off, the filtrate is evaporated and the residue is stirred with diethyl ether, 5.2 g. of crude product thus being obtained. This water-soluble product is recrystallized from methanolic diethyl ether to give 1-(N-acetylglycyl)-2-cyanoaziridine, which melts at 102°-104° C.

EXAMPLE 31

1-Hippuroyl-2-cyanoaziridine.

3.6 g. Hippuric acid and 1.36 g. 2-cyanoaziridine are dissolved in 36 ml. tetrahydrofuran and mixed, while cooling with ice, with 4.3 g. dicyclohexylcarbodiimide. After 2 hours, the dicyclohexylurea is separated off and the filtrate is evaporated. The residue is recrystallized from methylene chloride-ligroin to give 1.35 g. 1-hippuroyl-2-cyanoaziridine; m.p. 78°-81° C.

EXAMPLE 32

1-(Phthalimidoacetyl)-2-cyanoaziridine.

This compound is prepared in an analogous manner from 4.1 g. phthalimido acetic acid in a yield of 3.3 g.; m.p. 126°-128° C.

EXAMPLE 33

1-(DL-α-Acetylaminopropionyl)-2-cyanoaziridine.

This compound is prepared in an analogous manner from 3.9 g. acetylalanine. The product is a water-soluble oil.

EXAMPLE 34

1-(DL-α-Acetylaminophenylacetyl)-2-cyanoaziridine.

This compound is prepared in an analogous manner from 4.2 g. N-acetyl-DL-α-phenylglycine. After stirring the reaction mixture for 7 hours at ambient temperature, it is worked up in the usual manner. The yield is 1.3 g.; m.p. 96°-102° C.

EXAMPLE 35

1-(DL-α-Acetylamino-β-phenylpropionyl)-2-cyanoaziridine.

This compound is prepared in an analogous manner from 2.1 g. N-acetyl-DL-phenylalanine, the evaporation residue being crystallized from diethyl ether. The yield is 1.25 g.; m.p. 97°-109° C.

EXAMPLE 36

1-Benzyloxycarbonylglycyl-2-cyanoaziridine.

This compound is prepared in an analogous manner from 4 g. carbobenzoxyglycine. After working up the reaction mixture in the usual way, the product is obtained in the form of an oil, the yield being 3.7 g.

EXAMPLE 37

1-(N-p-Tosylglycyl)-2-cyanoaziridine.

This compound is prepared in an analogous manner from 4.6 g. N-p-tosylglycine and the reaction mixture worked up. The evaporation residue is stirred with diethyl ether to give 4.1 g. of the desired product; m.p. 124°-128° C.

EXAMPLE 38

1-(N-Trifluoroacetylglycyl)-2-cyanoaziridine.

This compound is obtained in an analogous manner from 3 g. N-trifluoroacetylglycine. There are obtained 3.7 g. of the desired product in the form of an oil.

EXAMPLE 39

1-(N-Acetyl-DL-leucyl)-2-cyanoaziridine.

3.4 g. N-Acetyl-Dl-leucine are suspended in 34 ml. tetrahydrofuran, 1.36 g. 2-cyanoaziridine is added thereto and the reaction mixture is then mixed with 4.4 g. dicyclohexylcarbodiimide, while stirring. After 2 hours in an ice bath, the reaction mixture is left to stand overnight at ambient temperature. Dicyclohexylurea is then filtered off and the filtrate is evaporated. After stirring the evaporation residue with diethyl ether, there are obtained 2.89 g. 1-(N-acetyl-DL-leucyl)-2-cyanoaziridine in the form of white crystals; m.p. 112°-116° C.

EXAMPLE 40

1-(DL-α-Acetamidoethoxymalonyl)-2-cyanoaziridine.

3.8 g. Monoethyl acetamidomalonate are suspended in 40 ml. diethyl ether, 1.36 g. 2-cyanoaziridine and 4.3 g. dicyclohexylcarbodiimide are added thereto and the reaction mixture is stirred for 2 hours in an ice bath. The dicyclohexylurea is then filtered off and the filtrate is evaporated to give 0.5 g. 1-(DL-α-acetamidoethoxymalonyl)-2-cyanoaziridine in the form of white crystals; m.p. 124°–127° C.

EXAMPLE 41

1-(2-Pyrrolidone-1-methylcarbonyl)-2-cyanoaziridine.

2.2 g. 2-Pyrrolidone-1-acetic acid are suspended in 44 ml. tetrahydrofuran and 1.05 g. 2-cyanoazridine and 3.3 g. dicyclohexylcarbodiimide are added thereto, with stirring and ice cooling. After 2 hours in an ice bath and 5 hours at ambient temperature, the dicyclohexylurea is filtered off and the filtrate evaporated. Crystallization of the evaporation residue from diethyl ether gives 2.5 g. of crystalline 1-(2-pyrrolidone-1-methylcarbonyl)-2-cyanoaziridine; m.p. 86°–90° C. (bubble formation).

EXAMPLE 42

1-(4-Methylbenzamidoacetyl)-2-cyanoaziridine.

In a manner analogous to Example 10, from 0.96 g. p-toluoylglycine (m.p. 161°–162° C.) and 0.34 g. 2-cyanoaziridine in 10 ml. tetrahydrofuran, after the addition of 1.08 g. dicyclohexylcarbodiimide at 10°–15° C., stirring for 30 minutes at 10°–15° C. and for 2 hours at ambient temperature and after filtering off with suction 1.1 g. dicyclohexylurea (m.p. 228° C.) and evaporation of the filtrate in a vacuum, there is obtained the desired compound in crude form. This is dissolved in ethyl acetate, the solution is shaken up with a saturated aqueous solution of sodium bicarbonate and the organic phase is dried and evaporated. The evaporation residue is repeatedly triturated with diethyl ether to give 0.95 g. 1-(4-methylbenzamidoacetyl)-2-cyanoaziridine; m.p. 92°–94° C.

EXAMPLE 43

1-(3,4-Methylenedioxybenzoyl)-2-cyanoaziridine.

A solution of 1.85 g. 3,4-methylenedioxybenzoyl chloride in 80 ml. anhydrous diethyl ether is added at 0° C. to a solution of 0.68 g. 2-cyanoaziridine and 1.2 g. triethylamine in 100 ml. anhydrous diethyl ether. The reaction mixture is stirred for 1 hour at 0° C. and then for 1 hour at ambient temperature, the precipitated hydrochloride is filtered off with suction, the ethereal filtrate is evaporated, the evaporation residue is triturated with 45 ml. diethyl ether and the crystals obtained are filtered off with suction to give 1.75 g. 1-(3,4-methylenedioxybenzoyl)-2-cyanoaziridine; m.p. 95°–97° C.

EXAMPLE 44

1-(N-Formylglycyl)-2-cyanoaziridine.

2.06 g. N-formylglycine are suspended in 20 ml. tetrahydrofuran, 1.36 g. 2-cyanoaziridine and 4.3 g. dicyclohexylcarbodiimide are added thereto, with ice cooling, and the reaction mixture is then stirred for 2 hours. After working up the reaction mixture in the usual manner, there is obtained 0.85 g. 1-(N-formylglycyl)-2-cyanoaziridine in the form of water-soluble crystals; m.p. 51°–56° C.

EXAMPLE 45

1-(N-Acetyl-N-methylglycyl)-2-cyanoaziridine.

In an analogous manner, from 2.6 g. N-acetylsarcosine there is prepared 1.7 g. 1-(N-acetyl-N-methylglycyl)2-cyanoaziridine in the form of a yellowish oil.

EXAMPLE 46

1-(N-Acetylglycylglycyl)-2-cyanoaziridine.

5.05 g. N-Acetylglycylglycine are dissolved in 60 ml. N,N-dimethylformamide and 2 g. 2-cyanoaziridine and 6.3 g. dicyclohexylcarbodiimide are added thereto, with ice cooling. After 2 hours in an ice bath and 2 hours at ambient temperature, the dicyclohexylurea is filtered off, the filtrate is evaporated in a vacuum and the evaporation residue is recrystallized from ethyl acetate to give 1.4 g. 1-(N-acetylglycylglycyl)-2-cyanoaziridine in the form of white, water-soluble crystals; m.p. 70°–76° C.

EXAMPLE 47

1-(N-Ethoxycarbonylglycyl)-2-cyanoaziridine.

In a manner analogous to Example 45, from 2.94 g. N-ethoxycarbonylglycine there are obtained 2.6 g. 1-(N-ethoxycarbonyglycyl)-2-cyanoaziridine in the form of water-soluble crystals; m.p. 55°–58° C.

EXAMPLE 48

1-(5-Acetylhydantoyl)-2-cyanoaziridine.

3 g. 5-Acetylhydantoic acid are suspended in 30 ml. tetrahydrofuran and 1.28 g. 2-cyanozridine is added thereto, as well as 4 g. dicyclohexylcarbodiimide, with ice cooling and stirring. After subsequently stirring for 4 hours in the cold and then leaving to stand overnight at ambient temperature, the dicyclohexylurea is filtered off and the filtrate is evaporated. After stirring the evaporation residue with diethyl ether, the residue crystallizes to give 2 g. 1-(5-acetylhydantoyl)2-cyanoaziridine; m.p. 118°–122° C.

EXAMPLE 49

1-(DL-2-N-Acetylglutaminyl)-2-cyanoaziridine.

In an analogous manner, from 3.8 g. N-acetylglutamine, 1.36 g. 2-cyanoaziridine and 4.4 g. dicyclohexylcarbodiimide in 38 ml. tetrahydrofuran, there is obtained 1-(DL-2-N-acetylgutaminyl)-2-cyanoaziridine in the form of an oil.

EXAMPLE 50

1-Hydantoyl-2-cyanoaziridine.

This compound is obtained in an analogous manner in a yield of 2 g. from 2.36 g. hydantoic acid; m.p. 110°–114° C.

EXAMPLE 51

1-(N-Benzenesulphonyl-N-n-propylglycyl)-2-cyanoaziridine.

2.6 g. N-Benzenesulphonyl-N-n-propylglycine are dissolved in 26 ml. diethyl ether, 0.68 g. 2-cyanoaziridine is added thereto, as well as 2.16 g. dicyclohexylcarbodiimide, with ice cooling. After working up the reaction mixture in the usual way, there are obtained 2.3 g. 1-(N-benzenesulphonyl-N-n-propylglycyl)-2-cyanoaziridine in the form of an oil.

EXAMPLE 52

1-N-β-Chloropropionylglycyl)-2-cyanoaziridine.

In an analogous manner, from 3.3 g. N-β-chloropropionylglycine in 33 ml. tetrahydrofuran, there is obtained 1.4 g. 1-(N-β-chloropropionylglycyl)-2-cyanoaziridine; m.p. 67°–72° C.

EXAMPLE 53

1-(DL-2-N-Acetylaminosuccinamoyl)-2-cyanoaziridine.

In an analogous manner, from 4.5 g. N-acetylasparagine there is obtained 1.2 g. 1-(DL-2-N-acetylaminosuccinamoyl)-2-cyanoaziridine in the form of a water-soluble, amorphous product.

EXAMPLE 54

1-(N-Acetyl-D-alanyl)-2-cyano(D- and L-)aziridine.

By replacing the racemic N-acetylalanine used in Example 33 by N-acetyl-D-alanine, $[\alpha]_D^{20} = +64°$, there is obtained, after separating off the dicyclohexylurea, a diastereomeric mixture which can be separated into the two forms by repeated recrystallization from diethyl ether.
Form A:
m.p. 109°–111° C. (recrystallized from diethyl ether)
thin layer chromatographically uniform;
$[\alpha]_D^{20} = +213.6°$ (c=1 in methanol)
Form B:
m.p. 87°–89° C. (recrystallized from acetone-ligroin, 1:1 v/v)
thin layer chromatographically uniform;
$[\alpha]_D^{20} = -166.0°$ (c=1 in methanol).

EXAMPLE 55

1-(N-Phenoxycarbonylglycyl)-2-cyanoaziridine.

In an analogous manner, from 3.9 g. N-phenoxycarbonylglycine in 40 ml. diethyl ether, there are obtained 2 g. 1-(N-phenoxycarbonyglycyl)-2-cyanoaziridine in the form of an oil.

EXAMPLE 56

1-(α-Acetylaminoisobutyryl)-2-cyanoaziridine.

This compound is obtained in an analogous manner from 5.4 g. α-acetylaminoisobutyric acid in 50 ml. tetrahydrofuran in the form of an oil. The product is purified on a silica gel column using the solvent mixture used in Example 25. The yield is 2.8 g.

EXAMPLE 57

1-(α-Phthalimidopropionyl)-2-cyanoaziridine.

This compound is obtained in an analogous manner from 2.5 g. α-phthalimidopropionic acid in 25 ml. tetrahydrofuran. The product is purified on a silica gel column with a mixture of heptane and methyl ethyl ketone (2:1 v/v). There is obtained 1.4 g. 1-(α-phthalimidopropionyl)-2-cyanoaziridine in the form of an oil.

EXAMPLE 58

1-(N-Acetyl-N-phenylglycyl)-2-cyanoaziridine.

In an analogous manner, from 3.86 g. N-acetyl-N-phenylglycine in 40 ml. tetrahydrofuran, there are obtained 3 g. 1-(N-acetyl-N-phenylglycyl)-2-cyanoaziridine in the form of white crystals; m.p. 69°–75° C.

EXAMPLE 59

1-(N-Acetyl-N-benzylglycyl)-2-cyanoaziridine.

In an analogous manner, from 4.14 g. N-acetyl-N-benzylglycine in 40 ml. tetrahydrofuran, there are obtained 3.9 g. 1-(N-acetyl-N-benzyglycyl)-2-cyanoaziridine in the form of an oil.

EXAMPLE 60

1-(N-Methoxyacetylglycyl)-2-cyanoaziridine.

2.94 g. N-Methoxyacetylglycine are dissolved in 29 ml. tetrahydrofuran and mixed, with stirring and ice cooling, with 1.36 g. 2-cyanoaziridine and 4.3 g. dicyclohexylcarbodiimide, whereafter the reaction mixture is stirred for 2 hours. After filtering off the dicyclohexylurea, from the filtrate there are obtained 2.8 g. of crystals which, for purification, are dissolved in ethyl acetate and reprecipitated with ligroin. There is thus obtained 1-(N-methoxyacetylglycyl)-2-cyanoaziridine; M.p. 70°–72° C.

EXAMPLE 61

1-(β-Acetylaminopropionyl)-2-cyanoaziridine.

This compound is obtained in an analogous manner, in the form of a water-soluble oil, from 2.6 g. β-acetylalanine, the yield being 1.7 g.

EXAMPLE 62

1-(4-Acetaminobutyryl)-2-cyanoaziridine.

This is obtained in an analogous manner from 4.4 g. 4-acetaminobutyric acid. The crystalline crude product (3.8 g.) is recrystallized from diethyl ether-methylene chloride and then melts at 72°–75° C.

EXAMPLE 63

1-(6-Acetylaminohexanoyl)-2-cyanoaziridine.

3.46 g. 6-Acetylaminohexanoic acid, 1.36 g. 2-cyanoaziridine and 4.3 g. dicyclohexylcarbodiimide are reacted in the usual manner in 35 ml. tetrahydrofuran and the reaction mixture then worked up to give 1.1 g. 1-(6-acetylaminohexanoyl)-2-cyanoaziridine which, after recrystallization from ethyl acetate-ligroin, melts at 74°–77° C.

EXAMPLE 64

1-Cyclohexylacetyl-2-cyanoaziridine.

A solution of 1.6 g. cyclohexylacetyl chloride in 10 ml. anhydrous diethyl ether is added dropwise at 0° C. to a solution of 0.68 g. 2-cyanoaziridine and 1.2 g. triethylamine in 30 ml. anhydrous diethyl ether. The reaction mixtur is then stirred for 1 hour at 0° C. and for 1 hour at ambient temperature. The precipitated hydrochloride (1.38 g.) is filtered off with suction, the filtrate is evaporated, the evaporation residue, dissolved in a little diethyl ether, is treated three times with 5 ml. amounts of water and the ethereal phase is dried and then evaporated, 1.62 g. 1-cyclohexylacetyl-2-cyanoaziridine being obtained in the form of an oil. The elementary analysis and the NMR and mass spectra confirm the structure of the product.

EXAMPLE 65

1-(2,4-Dichlorobenzoyl)-2-cyanoaziridine.

Analogously to Example 64, from 2.09 g. 2,4-dichlorobenzoyl chloride in 10 ml. diethyl ether and 0.68 g. 2-cyanoaziridine, as well as 1.2 g. triethylamine in 50 ml. anhydrous diethyl ether, there are obtained, without treatment with water, 2.2 g. of a semi-solid reaction product which, after trituration with about 4 ml. diethyl ether, gives 1.4 g. 1-(2,4-dichlorobenzoyl)-2-cyanoaziridine; m.p. 95°–97° C.

EXAMPLE 66

1-Cyclohexylcarbonyl-2-cyanoaziridine.

Analogously to Example 64, from 1.46 g. cyclohexanecarboxylic acid chloride, as well as 0.68 g. 2-cyanoaziridine and 1.2 g. triethylamine, there is obtained 1.45 g. 1-cyclohexylcarbonyl-2-cyanoaziridine in the form of an oil. The mass and NMR spectra confirm the structure of the product.

EXAMPLE 67

1-(N-p-Methoxybenzamidoacetyl)-2-cyanoaziridine.

1.04 g. N-p-Methoxybenzoylglycine (m.p. 173°–175° C.) is suspended in 10 ml. dry tetrahydrofuran, 0.34 g. 2-cyanoaziridine is added thereto and then 1.08 g. dicyclohexylcarbodiimide at a temperature of from 10° to 15° C. The reaction mixture is further stirred for 4 hours at this temperature, then filtered with suction and the solid subsequently washed into the filtrate with tetrahydrofuran and diethyl ether. The solid material thus obtained (1.1 g.; m.p. 224°–227° C.) is 1,3-dicyclohexylurea. The filtrate is evaporated in a vacuum and the evaporation residue is taken up in ethyl acetate. This solution is shaken with saturated aqueous sodium bicarbonate solution and the organic phase is separated off, dried and evaporated in a vacuum. The evaporation residue is again taken up in 15 ml. ethyl acetate and sufficient petroleum ether added thereto to precipitate out a greasy material. The liquid is poured off from the greasy material which is then repeatedly triturated with petroleum ether to give 0.85 g. 1-(N-p-methoxybenzamidoacetyl)-2-cyanoaziridine; m.p. 117°–120° C.

EXAMPLE 68

1-Carbamoylacetyl-2-cyanoaziridine.

2.15 g. Dicyclohexylcarbodiimide are introduced portionwise at 0° to 5° C. into a suspension of 1.03 g. carbamoylacetic acid and 0.68 g. 2-cyanoaziridine in 18 ml. tetrahydrofuran. The reaction mixture is stirred for 1 hour at 0° C. and then for 2 hours at ambient temperature. It is then filtered with suction and the solid material is washed with tetrahydrofuran and diethyl ether into the filtrate, 2.2 g. dicyclohexylurea (m.p. 226°–228° C.) being obtained. The filtrate is evaporated in a vacuum and the evaporation residue is triturated with ether to give 1.3 g. 1-carbamoylacetyl-2-cyanoaziridine; m.p. 115°–119° C.

EXAMPLE 69

1-(2-Thiophenecarbonyl)-2-cyanoaziridine.

Analogously to Example 4, from 1.47 g. thiophene-2-carbonyl chloride and 0.68 g. 2-cyanoaziridine, after stirring for 1 hour at 0° C. and for 30 minutes at ambient temerature (1.3 g. ammonium salt) and after evaporating the ethereal mother liquor, there is obtained 1.45 g. of an oil which is purified on a silica gel column (150 g. silica gel; chloroform as elution agent) to give 1.1 g. 1-(2-thiophenecarbonyl)-2-cyanoaziridine in the form of an oil, which solidifies after standing for a long time.

EXAMPLE 70

1-[3-(2-Furyl)-acryloyl]-2-cyanoaziridine.

A solution of 1.56 g. β-furyl-(2)-acryloyl chloride in 10 ml. anhyrous diethyl ether is added dropwise at 0° C. to a solution of 0.68 g. 2-cyanoaziridine and 1.2 g. triethylamine and 30 ml. anhydrous diethyl ether. The reaction mixture is stirred for 1 hour at 0° C. and for 1 hour at ambient temperature. The precipitated triethylammonium salt (1.28 g.) is filtered off with suction and the ethereal filtrate is concentrated to a volume of about 10 ml., shaken out three times with 4 ml. amounts of water and the ethereal phase is dried and evaporated, 1.56 g. of a dark brown oil being obtained. This is purified on a silica gel column (150 g. silica gel; chloroform as elution agent) to give 0.83 g. 1-[3-(2-furyl)-acryloyl]-2-cyanoaziridine in the form of an oil, which solidifies after standing for a long time.

The same compound is obtained by introducing 2.1 g. dicyclohexylcarbodiimide, dissolved in 10 ml. diethyl ether, at 0° C. into a solution of 1.38 g. β-(2-furyl)acrylic acid and 0.68 g. 2-cyanoaziridine in 30 ml. diethyl ether, stirring for 2 hours at 0° C. and leaving to stand overnight at ambient temperature; after analogous purification on a silica gel column, there is obtained 0.9 g. of an oil which solidifies after standing for several days. After trituration with petroleum ether, the compound melts at 59°–61° C.

EXAMPLE 71

1-(3-Chloropropionyl)-2-cyanoaziridine.

Analogously to Example 70, from 1.27 g. β-chloropropionyl chloride and 0.68 g. 2-cyanoaziridine or from β-chloropropionic acid, 2-cyanoaziridine and dicyclohexylcarbodiimide, without purification on a silica gel column, there is obtained 0.94 g. 1-(3-chloropropionyl)-2-cyanoaziridine in the form of a yellowish oil. The elementary analysis and the NMR and mass spectra confirm the structure of the product.

EXAMPLE 72

1-Stearoyl-2-cyanoaziridine.

A solution of 1.51 g. stearoyl chloride in 10 ml. anhydrous diethyl ether is added at 0° C. to a solution of 0.34 g. 2-cyanoaziridine and 0.6 g. triethylamine in 30 ml. anhydrous diethyl ether. The reaction mixture is stirred for 1 hour at 0° C. and for 1 hour at ambient temperature. The precipitated material is filtered off with suction, stirred up with 100 ml. ethyl acetate, filtered with suction (0.65 g. triethylammonium salt) and the ethyl acetate filtrate, together with the diethyl filtrate, evaporated. After trituration of the evaporation residue with diethyl ether, there is obtained 1.2 g. 1-stearoyl-2-cyanoaziridine; m.p. 85°–88° C.

EXAMPLE 73

1-Propionyl-2-cyanoaziridine.

A solution of 0.92 g. propionyl chloride in 40 ml. anhydrous diethyl ether is added dropwise at 0° to 5° C., in the course of about 15 minutes, to a solution of 0.68 g. 2-cyanoaziridine and 1.2 g. triethylamine in 40 ml. anhydrous diethyl ether. The reaction mixture is stirred for 1 hour at 0° C. and then for 2 hours at ambient temperature. The precipitated salt is filtered off with suction and washed with diethyl ether into the filtrate and the filtrate is evaporated in a vacuum to give 1.44 g. of an oil. This is dissolved in ethyl acetate, shaken with a saturated aqueous solution of sodium bicarbonate, dried and then evaporated in a vacuum. There is thus obtained 1.14 g. 1-propionyl-2-cyanoaziridine in the form of a pale oil, the analytical data (elementary analysis, NMR and mass spectra) of which confirm the structure. The product is slightly contaminated with water.

EXAMPLE 74

1-Phenoxyacetyl-2-cyanoaziridine.

Analogously to Example 73, from 1.7 g. phenoxyacetyl chloride and 0.68 g. 2-cyanoaziridine, there is obtained 1.45 g. 1-phenoxyacetyl-2-cyanoaziridine (m.p. 92°–94° C.). However, after the stirring, solid material is filtered off with suction (2.4 g.) and triturated with 70 ml. ethyl acetate, the remaining triethylammonium salt (1.2 g.) being filtered off with suction. The ethyl acetate solution is evaporated in a vacuum and the evaporation residue is triturated with diethyl ether. 0.85 g. of the desired compound are thus obtained (m.p. 92°–94° C.). A further 0.6 g. of the same compound (m.p. 92°–94° C.) is obtained by evaporation of the first diethyl ether filtrate and trituration of the evaporation residue with diethyl ether.

EXAMPLE 75

1-Phenylacetyl-2-cyanoaziridine.

1.28 g. of this compound (m.p. 76°–78° C.) are obtained analogously to Example 73 from 1.54 g. phenylacetyl chloride and 0.68 g. 2-cyanoaziridine but, after filtering off the triethylammonium chloride with suction and evaporating the ethereal filtrate, the evaporation residue obtained is triturated with diethyl ether, the desired product thus being obtained in crystalline form.

EXAMPLE 76

1-(4-Methylbenzoyl)-2-cyanoaziridine.

This compound is obtained in the form of an oil in a yield of 1.8 g. from 1.54 g. p-methylbenzoyl chloride and 0.68 g. 2-cyanoaziridine. It still contains a little ethyl acetate and water. The analytical results (elementary analysis, NMR and mass spectra) confirm the structure.

EXAMPLE 77

1-(2-Benzofuroyl)-2-cyanoaziridine.

This compound is obtained in a yield of 1.3 g., analogously to Example 75, from 1.8 g. benzofuran-2-carbonyl chloride and 0.68 g. 2-cyanoaziridine. It has a melting point of 92°–94° C.

EXAMPLE 78

1-(1-Methyl-3-nitropyrazole-4-carbonyl)-2-cyanoaziridine.

A solution of 1.89 g. 1-methyl-3-nitropyrazole-4-carboxylic acid chloride in 20 ml. anhydrous diethyl ether and 10 ml. anhydrous tetrahydrofuran is added dropwise at 0° to 5° C. to a solution of 0.68 g. 2-cyanoaziridine and 1.2 g. triethylamine in 15 ml. anhydrous diethyl ether. The reaction mixture is subsequently stirred for 2.5 hours at 0° C. and the liquid is then poured off from the resultant greasy material and evaporated in a vacuum. The oily evaporation residue thus obtained is taken up in ethyl acetate, the separated greasy material is triturated with this ethyl acetate solution, undissolved triethylammonium chloride is filtered off with suction, the ethyl acetate solution is shaken out with an aqueous solution of sodium bicarbonate, dried and the organic phase evaporated in a vacuum, 2.1 g. of oil remaining behind. This is repeatedly triturated with diethyl ether and finally with isopropanol, a viscous grease being formed which is left to stand overnight with isopropanol. There is thus obtained 1.1 g. 1-(1-methyl-3-nitropyrazole-4-carbonyl)-2-cyanoaziridine (m.p. 66°–72° C.), which is contaminated with a small amount of an isomeric compound with an opened aziridine ring.

EXAMPLE 79

1-(N-Ethoxycarbonyl-N-methyl-$\beta$-aminopropionyl)-2-cyanoaziridine.

3.5 g. N-Ethoxycarbonyl-N-methyl-$\beta$-aminopropionic acid are dissolved in 35 ml. tetrahydrofuran and, with stirring and ice cooling, 1.36 g. 2-cyanoaziridine and 4.3 g. dicyclohexylcarbodiimide are added thereto, whereafter stirring is continued for 2 hours. The precipitated dicyclohexylurea is then separated off and, after working up in the usual manner, there are obtained 3.7 g. 1-(N-ethoxycarbonyl-N-methyl-$\beta$-aminopropionyl)-2-cyanoaziridine in the form of an oil.

EXAMPLE 80

1-($\beta$-Phthalimidopropionyl)-2-cyanoaziridine.

2.5 g. $\beta$-Phthalimidopropionic acid are dissolved in 25 ml. dimethylformamide and, while stirring and cooling with ice, mixed with 2.46 g. dicyclohexylcarbodiimide, as well as with 0.78 g. 2-cyanoaziridine. The reaction mixture is subsequently stirred for 2 hours in an ice bath and for 4 hours at ambient temperature. After separating off the dicyclohexylurea, there is obtained a crude product which is recrystallized from ethyl acetate to give 1 g. 1-($\beta$-phthalimidopropionyl)-2-cyanoaziridine; m.p. 168°–170° C.

EXAMPLE 81

Succinyl-bis-(2-cyano-1-aziridine).

1.18 g. Succinic acid and 4.3 g. dicyclohexylcarbodiimide are dissolved in 50 ml. tetrahydrofuran, precipitation taking place after a short time. 1.36 g. 2-cyanoaziridine are then added thereto and the reaction mixture is stirred for 2 hours in an ice bath. After separating off the dicyclohexylurea, the filtrate is evaporated and the residue crystallized with diethyl ether to give 0.65 g. succinyl-bis-(-2-cyano-1-aziridine); m.p. 139°–144° C.

EXAMPLE 82

Decanedioyl-bis-(2-cyano-1-aziridine).

4 g. Sebacic acid are reacted with 2.7 g. 2-cyanoaziridine in an analogous manner. There is obtained 1 g. decanedioyl-bis-(2-cyano-1-aziridine) which, after recrystallization from ethyl acetate-ligroin, melts at 77°–82° C.

EXAMPLE 83

Ethanephosphono-bis-(2-cyano-1-aziridine).

1.36 g. 2-Cyanoaziridine and 2.78 ml. triethylamine are dissolved in 15 ml. anhydrous diethyl ether. A solution of 1.47 g. ethanephosphonic acid dichloride in 15 ml. anhydrous diethyl ether is added dropwise thereto, with stirring and ice cooling. After standing overnight at ambient temperature, the reaction mixture is filtered, the residue is washed with ethyl acetate and then this extract is evaporated and stirred with diethyl ether to give 0.85 g. ethanephosphono-bis-(2-cyano-1-aziridine) in the form of water-soluble crystals; m.p. 95° C.

EXAMPLE 84

DL-(2-N-Acetylaminosuccinyl)-1,4-bis-(2-cyano-1-aziridine).

A suspension of 4.5 g. N-acetylaspartic acid in a solution of 3.5 g. 2-cyanoaziridine and 11.1 g. dicyclohexylcarbodiimide in 45 ml. tetrahydrofuran is stirred for 2 hours in an ice bath and the reaction mixture then worked up in the usual manner. The oily evaporation residue obtained is purified on a silica gel column analogously to Example 25 to give 0.6 g. DL-(2-N-acetylaminosuccinyl)-1,4-bis-(2-cyano-1-aziridine) in the form of a water-soluble, amorphous product.

EXAMPLE 85

2-Cyano-1-(diethoxyphosphoryl)-aziridine.

A solution of 2.5 g. phosphoric acid diethyl ester chloride in 12 ml. anhydrous diethyl ether is added dropwise, with cooling, to a solution of 1.45 g. 2-cyanoaziridine and 3 ml. triethylamine in 14 ml. anhydrous diethyl ether. After 2 hours, the precipitated salt is separated off, washed with diethyl ether and the filtrate evaporated. The evaporation residue is purified on a silica gel column analogously to Example 25 to give 1.5 g. 2-cyano-1-(diethoxyphosphoryl)-aziridine in the form of a colorless oil.

EXAMPLE 86

1-(3-Chloropyridazine-6-mercaptoacetyl)-2-cyanoaziridine.

A solution of 2.28 g. 3-chloropyridazine-6-mercaptoacetic acid and 0.76 g. 2-cyanoaziridine in 25 ml. tetrahydrofuran is mixed, while cooling with ice, with 2.4 g. dicyclohexylcarbodiimide and then stirred for 2 hours. After standing overnight at ambient temperature, the precipitated dicyclohexylurea is filtered off with suction, the filtrate is evaporated in a vacuum and the residue is taken up in ethyl acetate. The solution is treated with charcoal and filtered, the filtrate is again evaporated and the residue obtained is stirred with diethyl ether. There is thus obtained 0.65 g. 1-(3-chloropyridazine-6-mercaptoacetyl)-2-cyanoaziridine; m.p. 104°–107° C.

EXAMPLE 87

1-(4-Ethoxycarbonylbenzoyl)-2-cyanoaziridine.

A solution of 2.18 g. p-ethoxycarbonylbenzoyl chloride in 20 ml. diethyl ether is added dropwise at 0° C. to a solution of 0.68 g. 2-cyanoaziridine and 1.2 g. triethylamine in 80 ml. diethyl ether. The reaction mixture is stirred for 1 hour at 0° C. and for 1 hour at ambient temperature. The precipitated triethylammonium salt is filtered off with suction, the filtrate is evaporated and the evaporation residue is triturated with diethyl ether to give 1.45 g. of a crude product (m.p. 82°–86° C.) which, after purification on a silica gel column (elution agent ethyl acetate; 110 g. silica gel) gives 1.3 g. 1-(4-ethoxycarbonylbenzoyl)-2-cyanoaziridine; m.p. 89°–91° C.

The same compound is obtained when a solution of 1.1 g. dicyclohexylcarbodiimide in 5 ml. diethyl ether is added at 0° C. to a mixture of 0.97 g. p-ethoxycarbonylbenzoic acid and 0.34 g. 2-cyanoaziridine in 15 ml. diethyl ether, stirred for 2 hours at this temperature and then for 1 hour at ambient temperature, the precipitated dicyclohexylurea is filtered off with suction (1.13 g.), the filtrate evaporated and the evaporation residue is triturated with about 3 ml. diethyl ether. The yield is 0.66 g.; m.p. 92°–94° C.

EXAMPLE 88

1-(N,N-Diethylsuccinamoyl)-2-cyanoaziridine.

3.46 g. N,N-Diethylsuccinic acid monoamide and 4.3 g. dicyclohexylcarbodiimide are dissolved in 35 ml. tetrahydrofuran and 1.36 g. 2-cyanoaziridine is added to the resultant suspension. After subsequently stirring for 2 hours in an ice bath and leaving to stand overnight at ambient temperature, the dicyclohexylurea is separated off and the filtrate evaporated. There are thus obtained 2.9 g. 1-(N,N-diethylsuccinamoyl)-2-cyanoaziridine in the form of an oil.

EXAMPLE 89

1-[N-(Furan-2-carbonyl)-glycyl]-2-cyanoaziridine.

2.15 g. Dicyclohexylcarbodiimide are slowly added at 0° to 5° C. to a mixture of 1.69 g. N-(2-furoyl)-glycine and 0.68 g. 2-cyanoaziridine in 18 ml. tetrahydrofuran. The reaction mixture is stirred for 1 hour at 0° C. and for 3 hours at ambient temperature. The precipitated dicyclohexylurea is filtered off with suction (2.2 g.; m.p. 229° C.), the filtrate is evaporated in a vacuum and the oily evaporation residue is repeatedly triturated with diethyl ether to give 1.3 g. 1-[N-(furan-2-carbonyl)-glycyl]-2-cyanoaziridine; m.p. 98°–100° C.

The N-(2-furoyl)-glycine used as starting material is prepared as follows: 2.5 g. aminoacetic acid, 0.8 g. solid sodium hydroxide, 2 g. anhydrous sodium carbonate and 20 ml. water are mixed dropwise at 10°–15° C. with 2.6 g. furan-2-carboxylic acid chloride. The reaction mixture is stirred for 2.5 hours at 15° C., 8 ml. concentrated hydrochloric acid are then added thereto, with ice cooling, the reaction mixture is left to stand for about 30 minutes in an ice bath and the precipitated material is filtered off with suction and washed with water to give 2.5 g. N-(α-furoyl)-aminoacetic acid; m.p. 166°–168° C.

EXAMPLE 90

1-n-Butylsulphinylacetyl-2-cyanoaziridine.

A solution of 2.93 g. m-chlorobenzoic acid in 20 ml. chloroform is added dropwise at ambient temperature to a solution of 2.8 g. of 1-n-butylthioacetyl-2-cyanoaziridine (see Example 7) in 60 ml. chloroform. The reaction mixture is then stirred for 2 hours at ambient temperature, evaporated in a vacuum to a volume of about 40 ml. and shaken out three times with 3 ml. amounts of aqueous sodium bicarbonate solution. The organic phase is dried and the chloroform is evaporated off to give 2.64 g. 1-n-butylculphinylacetyl-2-cyanoaziridine in the form of an oil. After purification on a column of 150 g. silica gel (elution agent ethyl acetate), there is obtained 1.07 g. of thin layer chromatographically uniform product in the form of a viscous, yellowish oil. The analytical data (elementary analysis, NMR and mass spectra) confirm the structure.

EXAMPLE 91

1-Cyclopropylcarbonyl-2-cyanoaziridine.

1.34 g. of this compound are obtained in the form of an oil when, analogously to Example 87, 1.36 g. 2-cyanoaziridine and 2.2 g. triethylamine in 30 ml. diethyl ether are reacted with 2.09 g. cyclopropane-carboxylic acid chloride, the ethereal filtrate obtained after separating off the triethylamine hydrochloride is shaken out three times with 4 ml. amounts of water and the ethereal phase is dried and evaporated. After purifying 1 g. thereof on a column of 100 g. silica gel, using chloroform as elution agent, there is obtained 0.5 g. of the desired compound in the form of an oil. The analytical data (elementary analysis, NMR and mass spectra) confirm the structure.

EXAMPLE 92

1-Cyclopropane-carbonamidoacetyl-2-cyanoaziridine.

This compound is obtained in a yield of 0.75 g. (m.p. 116°–118° C.) analogously to Example 89 by reacting 0.71 g. cyclopropylcarbonylglycine (m.p. 128°–130° C.) and 0.34 g. 2-cyanoaziridine in 9 ml. tetrahydrofuran with 1.08 g. dicyclohexylcarbodiimide.

The preparation of the cyclopropanecarbonylglycine used as starting material also takes place in the manner described in Example 89 from cyclopropanecarboxylic acid chloride and aminoacetic acid.

EXAMPLE 93

1-(2-Methylthiazole-5-carbonyl)-2-cyanoaziridine.

1.6 g. 2-Methylthiazole-5-carboxylic acid (m.p. 209° C.) and 0.76 g. 2-cyanoaziridine in 20 ml. tetrahydrofuran are mixed at 0° to 5° C. with 2.4 g. dicyclohexylcarbodiimide. The reaction mixture is stirred for 1 hour at 0° C. and for 3 hours at ambient temperature, whereafter the precipitated dicyclohexylurea is filtered off with suction and washed with the above-mentioned solvent and with diethyl ether. The filtrate is evaporated in a vacuum and the evaporation residue is taken up in ethyl acetate and shaken out with a saturated aqueous solution of sodium bicarbonate. The organic phase is dried and evaporated in a vacuum to give 2.38 g. of an oil. This oily residue is dissolved in 90 ml. diethyl ether, left to stand overnight, precipitated dicyclohexylurea is filtered off with suction, the ethereal solution is evaporated and the evaporation residue is triturated with a little diethyl ether, 1.4 g. 1-(2-methylthiazole-5-carbonyl)-2-cyanoaziridine being obtained; m.p. 90°–92° C.

EXAMPLE 94

1-[1-(6-Pyridazonyl)-acetyl]-2-cyanoaziridine 3.5 g. 1-(6-Pyridazonyl)-acetic acid are suspended in 35 ml. tetrahydrofuran, 1.55 g. 2-cyanoaziridine are added thereto, as well as, with ice cooling, 4.91 g. dicyclohexylcarbodiimide. After further stirring the reaction mixture for 2 hours in an ice bath, it is allowed to come to ambient temperature and the dicyclohexylurea is filtered off and the filtrate evaporated. The crystalline residue is triturated with diethyl ether and filtered off with suction. There are obtained 3.85 g. 1-[1-(6-pyridazonyl)-acetyl]-2-cyanoaziridine in the form of white crystals; m.p. 87°–91° C.

EXAMPLE 95

1-(3,4,5-Trimethoxybenzoyl)-2-cyanoaziridine

In a manner analogous to that described in Example 94 with the use of 3,4,5-trimethoxybenzoic acid as starting material, there is obtained 1-(3,4,5-trimethoxybenzoyl)-2-cyanoaziridine; m.p. 86°–89° C.

EXAMPLE 96

1-Acryloylamidoacetyl-2-cyanoaziridine

A solution of 2.06 g. dicyclohexylcarbodiimide in 5 ml. diethyl ether is added dropwise at 0° C. to a suspension of 1.29 g. N-acryloylglycine (m.p. 128°–131° C.) and 0.68 g. 2-cyanoaziridine in 25 ml. diethyl ether. The reaction mixture is stirred for 2 hours at 0° C. and then left to stand overnight at ambient temperature. The precipitated crystals (3.25 g.) are filtered off with suction, stirred with 30 ml. ethyl acetate and the dicyclohexylurea, which remains undissolved, is filtered off with suction. The ethyl acetate filtrate is evaporated in a vacuum and the oily evaporation residue is triturated with diethyl ether to give 0.63 g. 1-acryloylamidoacetyl-2-cyanoaziridine, which melts at 125°–126° C.

EXAMPLE 97

N,N'-Terephthaloyl-bis-1-(2-cyanoaziridine)

A solution of 2.03 g. terephthalic acid dichloride in 20 ml. anhydrous diethyl ether is added dropwise at 0° to 5° C. to a mixture of 1.36 g. 2-cyanoaziridine, 2.4 g. triethylamine and 60 ml. anhydrous diethyl ether. The reaction mixture is then stirred for 1 hour at 0° C. and for 2 hours at ambient temperature, whereafter the solid product (5.3 g.) is filtered off with suction, this finely powdered material is shaken up with 100 ml. dioxan at 60° C., undissolved material is filtered off with suction, the dioxan filtrate is evaporated in a vacuum and the evaporation residue is triturated with diethyl ether to give 2.1 g. of crystals. These crystals are triturated with a saturated aqueous solution of sodium bicarbonate and the crystals obtained are filtered off with suction and washed with water to give 1.8 g. N,N'-terephthaloyl-bis-1-(2-cyanoaziridine); m.p. 168°–170° C.

EXAMPLE 98

1-Propionyl-2-cyanoaziridine 1.95 g. Propionic anhydride is added dropwise at ambient temperature to a mixture of 0.68 g. 2-cyanoaziridine in 5 ml. anhydrous diethyl ether. The reaction mixture is then stirred for 4 hours at this temperature, whereafter the solution is added dropwise to a well stirred mixture of 5 g. sodium bicarbonate in 50 ml. water, repeatedly extracted with ethyl acetate and the combined extracts evaporated in a vacuum, 1.6 g. of residue being obtained. This is treated with a suspension of 5 g. sodium bicarbonate in 30 ml. water, well stirred for 30 minutes, the undissolved sodium bicarbonate is filtered off with suction, the filtrate is repeatedly extracted with ethyl acetate and this then evaporated in a vacuum to give 0.85 g. 1-propionyl-2-cyanoaziridine, which is identical to the product of Example 73 (according to the thin layer chromatogram and the mass and NMR spectra).

EXAMPLE 99

1-[N-Pyridone-(2)-acetyl]-2-cyanoaziridine 3.06 g. N-Pyridone-(2)-acetic acid, 1.36 g. 2-cyanoaziridine and 4.3 g. dicyclohexylcarbodiimide are mixed in 31 ml. tetrahydrofuran, with stirring and ice cooling. After 2 hours, the reaction mixture is allowed to warm up to ambient temperature and filtered off from dicyclohexylurea. The filtrate is evaporated and the evaporation residue is taken up in butyl acetate, filtered, mixed with ligroin and the precipitated greasy material is crystallized from diethyl ether to give 2.9 g. 1-[N-pyridone-(2)-acetyl]-2-cyanoaziridine; m.p. 97°–102° C. (bubble formation).

EXAMPLE 100

1-(1-Methyl-3-nitropyrazole-4-carbonylglycyl)-2-cyanoaziridine 1.14 g. N-(1-Methyl-3-nitropyrazole-4-carbonyl)-glycine (m.p. 159°–161° C.) is dissolved in 70 ml. hot tetrahydrofuran and 0.34 g. 2-cyanoaziridine is added thereto, followed by the portionwise addition of 1.5 g. dicyclohexylcarbodiimide at 25°–30° C., whereafter the reaction mixture is stirred for 5 hours at ambient temperature and left to stand overnight. The precipitated dicyclohexylurea is filtered off with suction and the filtrate evaporated in a vacuum. The evaporation residue (2.65 g. of an oil) is, after standing for 30 minutes, triturated with 10 ml. tetrahydrofuran to give 0.45 g. 1-(1-methyl-3-nitropyrazole-4-carbonylglycyl)-2-cyanoaziridine in the form of a crystalline material; m.p. 158°–160° C. From the mother liquor there is obtained, by renewed evaporation and trituration, a further 0.3 g. of the desired product which still contains some dicyclohexylurea. It is, therefore, dissolved in warm ethyl acetate, left to stand overnight at ambient temperature, the precipitated dicyclohexylurea is filtered off with suction, the ethyl acetate mother liquor is evaporated and the residue again triturated.

The N-(12-cyanoaziridine 3-nitropyrazole-4-carbonyl)-glycine used as starting material is prepared analogously to Example 89 from 3.8 g. 1-methyl-3-nitropyrazole-4-carboxylic acid and 2.5 g. aminoacetic acid, the yield being 3.8 g.

EXAMPLE 101

1-(m-Trifluoromethylbenzoyl)-2-cyanoaziridine 2.15 g. Dicyclohexylcarbodiimide are introduced portionwise at 0° to 5° C. into a mixture of 1.9 g. m-trifluoromethylbenzoic acid and 0.68 g. 2-cyanoaziridine in 18 ml. tetrahydrofuran. The reaction mixture is subsequently stirred for 1 hour at 0° C. and for 3 hours at ambient temperature, the precipitated dicyclohexylurea is filtered off with suction, the mother liquor is evaporated in a vacuum, the evaporation residue is taken up in 50 ml. anhydrous diethyl ether and left to stand for 3 days at ambient temperature, filtered off with suction from further dicyclohexylurea and the filtrate repeatedly washed with 15 ml. amounts of water. The dried ethereal phase is evaporated, 2.7 g. of evaporation residue being obtained. This is triturated with a little diethyl ether, suction filtered from some crystalline by-product and the mother liquor is evaporated to give 2.2 g. 1-(m-trifluoromethylbenzoyl)-2-cyanoaziridine in the form of an oil. After purification on a silica gel column (about 120 fold amount of silica gel, using chloroform as elution agent), there is obtained 0.65 g. of thin layer chromatographically uniform product.

The same product can also be obtained from m-trifluoromethylbenzoyl fluoride and 2-cyanoaziridine in a manner analogous to that described in Example 43.

EXAMPLE 102

1-Phenylsulphenyl-2-cyanoaziridine

A solution of 1.44 g. benzenesulphenic acid chloride (b.p. 38°–40° C./0.2 mm.Hg) in 40 ml. anhydrous diethyl ether is added dropwise at 0° to 5° C. in the course of about 15 minutes to a mixture of 0.68 g. 2cyanoaziridine and 1.2 g. triethylamine in 40 ml. anhydrous diethyl ether. The reaction mixture is subsequently stirred for 1 hour at 0° C. and for 2 hours at ambient temperature. The precipitated hydrochloride is filtered off with suction, the mother liquor is evaporated in a vacuum and the evaporation residue is taken up in ethyl acetate and shaken out with an aqueous solution of sodium bicarbonate. The organic phase is evaporated to give 1.4 g. of oily evaporation residue which is vigorously shaken out 4 times with 20 ml. amounts of petroleum ether, 0.9 g. 1-phenylsulphenyl-2-cyanoaziridine remaining in the form of an oil which still contains a little diphenyl sulphide. The elementary analysis and the NMR, mass and IR spectra confirm the structure.

EXAMPLE 103

1-(2-Methylsulphinylbenzoyl)-2-cyanoaziridine

This compound, which melts at 143°–145° C., is obtained analogously to Example 90 from 0.44 g. 1-(2-methylthiobenzoyl)-2-cyanoaziridine, again with column purification. The yield is 0.15 g.

EXAMPLE 104

1-n-Butylthioacetylglycyl-2-cyanoaziridine.

A solution of 0.34 g. 2-cyanoaziridine in 5 ml. diethyl ether is added dropwise at 0° C. to a suspension of 1.025 g. n-butylthioacetylglycine (m.p. 80°–82° C.) and 1.03 g. dicyclohexylcarbodiimide in 25 ml. diethyl ether. The reaction mixture is stirred for 1 hour at 0° C. and for 1 hour at ambient temperature and the resultant dicyclohexylurea (1.1 g.; m.p. 226°–230° C.) is filtered off with suction. The ethereal solution is concentrated in a vacuum to about 10 ml., shaken out twice with 2 ml. amounts of water and the ethereal phase then dried and evaporated to give 0.90 g. 1-n-butylthioacetylglycol-2-cyanoaziridine in the form of a yellow oil. The elementary analysis and the mass and NMR spectra confirm the structure. The product still contains a little n-butylthioacetylglycine.

The n-butylthioacetylglycine used as starting material is obtained, in a yield of 2.4 g., from 3.4 g. n-butylthioacetyl chloride and 2.5 g. aminoacetic acid in a manner analogous to that described in Example 89.

EXAMPLE 105

1-(p-Phenylbenzoyl)-2-cyanoaziridine.

A solution of 1.08 g. p-phenylbenzoyl chloride in 30 ml. anhydrous diethyl ether is added dropwise at 0° to 5° C. in the course of about 15 minutes to a mixture of 0.34 g. 2-cyanoaziridine and 0.6 g. triethylamine in 20 ml. anhydrous diethyl ether. The reaction mixture is then stirred for 1 hour at 0° C. and for 2 hours at ambient temperature. The precipitated material is filtered off with suction, washed with diethyl ether into the filtrate and the clear ethereal mother liquor is evaporated. The evaporation residue is triturated with a little diethyl ether to give 0.7 g. 1-(p-phenylbenzoyl)-2-cyanoaziridine; m.p. 104°–106° C.

EXAMPLE 106

1-(2-Methylsulphonylbenzoyl)-2-cyanoaziridine.

A solution of 2.18 g. crude 2-methylsulphonylbenzoyl chloride (obtained from 6 g. 2-methylsulphonylbenzoic acid and 12 ml. thionyl chloride by boiling under reflux for 3 hours and then evaporating off excess thionyl chloride) in 20 ml. dioxan is added dropwise at 10° to 15° C. to a solution of 1.2 g. triethylamine and 0.68 g. 2-cyano-aziridine in 20 ml. dioxan. The reaction mixture is stirred for 1 hour at this temperature and then for 1 hour at ambient temperature. The resultant triethylammonium chloride (1.29 g.) is filtered off with suction and the mother liquor is evaporated in a vacuum. The evaporation residue is triturated with isopropanol to give 1.1 g. of product (m.p. 126°–130° C.) which, after dissolving in ethyl acetate, washing the solution with an aqueous solution of sodium bicarbonate and evaporating the ethyl acetate in a vacuum, gives 0.4 g. 1-(2-methylsulphonylbenzoyl)-2-cyanoaziridine; m.p. 135°–137° C.

EXAMPLE 107

1-(Phenylthioacetyl)-2-cyanoaziridine.

A solution of 1.68 g. phenylthioacetic acid in 20 ml. diethyl ether is added dropwise at 0° C. to a solution of 0.68 g. 2-cyanoaziridine and 2.1 g. dicyclohexylcarbodiimide in 10 ml. diethyl ether. The reaction mixture is stirred for 1 hour at 0 ° C. and for 2 hours at ambient temperature. The precipitated dicyclohexylurea (2.1 g.) is filtered off with suction and the mother liquor is concentrated to a volume of about 10 ml. and repeatedly shaken out with an aqueous solution of sodium bicarbonate and then with water. The ethereal phase is evaporated to give 0.8 g. 1-(phenylthioacetyl)-2-cyanoaziridine in the form of a yellowish oil. The elementary analysis and the NMR and mass spectra confirm the structure.

EXAMPLE 108

1-(N-Acetylmethionyl)-2-cyanoaziridine.

A solution of 0.412 g. dicyclohexylcarbodiimide in 5 ml. diethyl ether is added dropwise, with stirring, at 0° C. to a suspension of 0.38 g. N-acetyl-DL-methionine and 0.136 g. 2-cyanoaziridine in 10 ml. diethyl ether. The reaction mixture is then stirred for 1 hour at 0° C. and for 2 hours at ambient temperature and then left to stand overnight at ambient temperature. The resultant dicyclohexylurea is now filtered off with suction, the mother liquor is evaporated and the evaporation residue is triturated with about 3 ml. diethyl ether to give 0.35 g. 1-(N-acetylmethonyl)-2-cyanoaziridine; m.p. 86°–88° C.

EXAMPLE 109

1-p-Ethoxycarbonylamidobenzoyl)-2-cyanoaziridine.

A solution of 2.27 g. ethoxycarbonylamidobenzoyl chloride in 50 ml. diethyl ether is added dropwise at 0° C. to a solution of 0.68 g. 2-cyanoaziridine and 1.2 g. triethylamine in 50 ml. diethyl ether. The reaction mixture is then stirred for 1 hour at 0° C. and for 2 hours at ambient temperature and the resultant crystals (2.9 g.) are filtered off with suction and the mother liquor is evaporated. The crystals filtered off (2.9 g.) are triturated with 20 ml. ethyl acetate, 1.27 g. triethylammonium chloride thereby remaining undissolved. The ethyl acetate mother liquor is diluted with 30 ml. ethyl acetate, repeatedly shaken out with 5 ml. amounts of aqueous sodium bicarbonate solution and the organic phase then evaporated in a vacuum to give 0.6 g. 1-p-ethoxy-carbonylamidobenzoyl-2-cyanoaziridine; m.p. 137°–139° C. From the evaporation residue of the ethereal mother liquor there is obtained a further 0.49 g. of the desired product with the same melting point when this is dissolved in about 20 ml. ethyl acetate, the solution shaken out three times with 5 ml. amounts of aqueous sodium bicarbonate solution and the organic phase then evaporated in a vacuum.

EXAMPLE 110

1-(3-Cyclohexenecarbonyl)-2-cyanoaziridine.

Analogously to Example 107, from 1.36 g. 2-cyanoaziridine and 4.2 g. dicyclohexylcarbodiimide in 40 ml. diethyl ether and 2.52 g. 3-cyclohexene-1-carboxylic acid in 20 ml. diethyl ether, there are obtained 2.07 g. 1-(3-cyclohexenecarbonyl)-2-cyanoaziridine in the form of an oil from which, by dissolving in 5 ml. diethyl ether and leaving to stand for 12 hours at ambient temperature, a further small amount of dicyclohexylurea can be separated. Evaporation of the ethereal mother liquor leaves behind 1.8 g. of a yellow oil which still contains a little dicyclohexylurea. The elementary analysis and the NMR and mass spectra confirm the structure.

EXAMPLE 111

1-(4-Cyanobenzoyl)-2-cyanoaziridine.

A solution of 1.65 g. 4-cyanobenzoyl chloride in 25 ml. diethyl ether is added dropwise at 0° C. to a solution of 0.68 g. 2-cyanoaziridine and 1.2 g. triethylamine in 65 ml. diethyl ether. The reaction mixture is stirred for 1 hour at 0° C. and for 2 hours at ambient temperature. The precipitated triethylammonium chloride is filtered off with suction, the ethereal mother liquor is evaporated and the evaporation residue is triturated with diethyl ether. After purification on a silica gel column using chloroform as elution agent, there is obtained 0.6 g. 1-(4-cyanobenzoyl)-2-cyanoaziridine in the form of a white powder; m.p. 107°–110° C.

EXAMPLE 112

1-(Phenylthioacetamidoacetyl)-2-cyanoaziridine.

2.2 g. Dicyclohexylcarbodiimide are added portionwise at 0° to 5° C. to a mixture of 2.25 g. N-phenylthioacetylglycine (m.p. 118°–120° C.), 18 ml. tetrahydrofuran and 0.68 g. 2-cyanoaziridine. The reaction mixture is stirred for 1 hour at 0° C. and for 3 hours at ambient temperature. The precipitated dicyclohexylurea (2.18 g.; m.p. 226°–228° C.) is filtered off with suction, washed with tetrahydrofuran and then with diethyl ether into the filtrate, this then evaporated in a vacuum and the oily evaporation residue repeatedly triturated with diethyl ether. The oil which remains undissolved in the diethyl ether is taken up in 30 ml. ethyl acetate, left to stand overnight at ambient temperature, a small amount of crystalline material is filtered off with suction and the filtrate is evaporated in a vacuum, 1.6 g. 1-(phenylthioacetamidoacetyl)-2-cyanoaziridine remaining behind in the form of a yellowish oil which still contains a small amount of ethyl acetate. The elementary analysis and the NMR and mass spectra confirm the structure.

The N-phenylthioacetylglycine used as starting material is prepared as follows: 2.5 g. glycine in 20 ml. water, which contains 0.8 g. sodium hydroxide and 2 g. anhydrous sodium carbonate, are mixed dropwise at 10° to 15° C. with 3.73 g. phenylthioacetyl chloride. The reaction mixture is stirred for 2.5 hours at this temperature, then 8 ml. concentrated hydrochloric acid are added, with cooling. The precipitated substance is filtered off with suction after standing for 30 minutes and washed with water to give 4.3 g. N-phenylthioacetylglycine; m.p. 118°–120° C.

EXAMPLE 113

1-(2-Phenylcyclopropane-1-carbonyl)-2-cyanoaziridine.

A solution of 1.8 g. 2-phenylcyclopropane-1-carbonyl chloride in 10 ml. diethyl ether is added dropwise at 0° C. to a solution of 1.2 g. triethylamine and 0.68 g. 2-cyanoaziridine in 20 ml. diethyl ether. The reaction mixture is stirred for 1 hour at 0° C. and for 2 hours at ambient temperature. The precipitated triethylamine hydrochloride (1.36 g.) is filtered off with suction and the ethereal filtrate is concentrated to a volume of about 20 ml., then repeatedly shaken out with about 3 ml. amounts of water and the ethereal phase evaporated to give 1.43 g. of a yellow oil. This is purified on a 300 g. silica gel column, using chloroform as elution agent, there being obtained 0.83 g. 1-(2-phenylcyclopropane-1-carbonyl)-2-cyanoaziridine in the form of a yellow oil. The elementary analysis and the NMR and mass spectra confirm the structure.

EXAMPLE 114

1(5-Norbornene-2-carbonyl)-2-cyanoaziridine.

Analogously to Example 113, from 0.68 g. 2-cyanoaziridine and 1.2 g. triethylamine in 30 ml. diethyl ether and 1.56 g. 5-norbornene-2-carboxylio acid chloride in 10 ml. diethyl ether, after filtering off with suction the triethylammonium salt (1.25 g.), shaking out the ethereal filtrate three times with 5 ml. amounts of aqueous sodium bicarbonate solution and evaporating the ethereal solution, there is obtained 1.82 g. 1-(5-norbornene-2-carbonyl)-2-cyanoaziridine in the form of a yellow oil. The elementary analysis and the IR and mass spectra confirm the structure.

EXAMPLE 115

1-(2-Acetoxybenzoyl)-2-cyanoaziridine.

Analogously to Example 113, from 1.36 g. 2-cyanoaziridine and 2.4 g. triethylamine in 60 ml. diethyl ether and 3.96 g. of 2-acetoxybenzoyl chloride in 20 ml. diethyl ether, after filtering off with suction the precipitated triethylammonium salt (2.62 g.), shaking out the ethereal filrate three times with 10 ml. amounts of aqueous sodium bicarbonate solution, evaporating the ethereal phase and purifying the oil obtained on a silica gel column, using chloroform as elution agent, there is obtained 1.27 g. 1-(2-acetoxybenzoyl)-2-cyanoaziridine in the form of a water-clear, viscous oil which still contains a small amount of water. The elementary analysis and the IR, NMR and mass spectra confirm the structure.

EXAMPLE 116

1-(N-Acetylprolyl)-2-cyanoaziridine.

A solution of 2.06 g. dicyclohexylcarbodiimide in 10 ml. diethyl ether is added dropwise at 0° C. to a suspension of 1.57 g. L-N-acetylproline (m.p. 116°–118° C.) and 0.68 g. 2-cyanoaziridine in 40 ml. diethyl ether. The reaction mixture is stirred for 1 hour at 0° C. and for 2 hours at ambient temperature. The precipitated dicyclohexylurea (1.96 g.) is filtered off with suction, the filtrate is shaken out three times with 5 ml. amounts of water and the combined aqueous extracts are extracted three times with 10 ml. amounts of ethyl acetate, there thus being obtained 1.2 g. 1-(N-acetylproyly)-2-cyanoaziridine in the form of a yellowish, viscous oil. The elementary analysis and the NMR and mass spectra confirm the structure.

EXAMPLE 117

1-Benzylthioacetyl-2-cyanoaziridine.

Analogously to Example 116, from 1.82 g. benzylthioacetic acid and 0.68 g. 2-cyanoaziridine dissolved in 40 ml. diethyl ether and 2 g. dicyclohexylcarbodiimide in 30 ml. diethyl ether but after subsequently stirring for 3 hours at ambient temperature and filtering off with suction the dicyclohexylurea, washing the ethereal mother liquor with aqueous sodium bicarbonate solution and water, evaporating the ethereal phase to a volume of about 40 ml., leaving to stand overnight, filtering off with suction further dicyclohexylurea and evaporating the filtrate, there are obtained 2.12 g. 1-benzylthioacetyl-2-cyanoaziridine in the form of a viscous, colorless oil which still contains a small amount of dicyclohexylurea. The elementary analysis and the IR, NMR and mass spectra confirm the structure.

EXAMPLE 118

1-(3-Ethoxypropionyl)-2-cyanoaziridine.

Analogously to Example 113, from 0.68 g. 2-cyanoaziridine and 1.2 g. triethylamine in 40 ml. diethyl ether and 1.36 g. ethoxypropionyl chloride in 40 ml. diethyl ether, filtering off with suction 1.36 g. of hydrochloride evaporating the filtrate to one half of its volume and washing with aqueous sodium bicarbonate solution and water there is obtained 1 g. 1-(3-ethoxypropionyl)-2-cyanoaziridine in the form of a yellowish oil. The elementary analysis and the IR, NMR and mass spectra confirm the structure.

EXAMPLE 119

1-N,N-p-Dimethylaminobenzoyl)-2-cyanoaziridine.

Analogously to Example 113, from 0.34 g. 2-cyanoaziridine and 0.6 g. triethylamine in 20 ml. diethyl ether and the proportion of 0.92 crude p-dimethylaminobenzoyl chloride which dissolves in 20 ml. diethyl ether but after stirring for 3 hours at ambient temperature, there is obtained 0.3 g. 1-(N,N-p-dimethylaminobenzoyl)-2-cyanoaziridine; m.p. 104°–106° C.

EXAMPLE 120

1-(6-Methylpyridine-2-carbonyl)-2-cyanoaziridine.

An ethereal solution of 6-methylpyridine-2-carbonyl chloride (prepared by introducing 1.37 g. 6-methylpyridine 2-carboxylic acid into 27 ml. thionyl chloride, heating to 80° C. until a clear solution is obtained (about 1 hour), distilling off excess thionyl chloride in a vacuum at about 30° to 40° C. bath temperature and taking up the residue in 30 ml. diethyl ether) is added dropwise at 0° C. to a solution of 0.68 g. 2-cyanoaziridine and 2.4 g. triethylamine in 20 ml. diethyl ether. The reaction mixture is stirred for 1 hour at 0° C. and for 2 hours at ambient temperature. The precipitated hydrochloride is filtered off with suction, the ethereal filtrate is evaporated and the evaporation residue (0.9 g.) is triturated with about 4 ml. diethyl ether to give 0.4 g. 1-(6-methylpyridine-2-carbonyl)-2-cyanoaziridine; m.p. 120°–122° C.

EXAMPLE 121

1-[2-(4-Chlorobenzoyl)-benzoyl]-2-cyanoaziridine.

2.6 g. 2-(p-chlorobenzoyl)-benzoic acid are dissolved in 30 ml. diethyl ether, 0.68 g. 2-cyanoaziridine are added thereto and a solution of 2 g. dicyclohexylcarbodiimide in 20 ml. diethyl ether is added dropwise thereto at 0° to 5° C. in the course of about 10 minutes. The reaction mixture is subsequently stirred for 1 hour at 0° C. and for 4 hours at ambient temperature, precipitated dicyclohexylurea (2.2 g.) is filtered off with suction and the ethereal filtrate is shaken out with an aqueous solution of sodium bicarbonate and repeatedly with water. The ethereal phase is evaporated to give 3 g. 1-[2-(4-chlorobenzoyl)-benzoyl]-2-cyanoaziridine in the form of a colorless viscous oil which still contains small amounts of dicyclohexylurea. The elementary analysis and the IR, NMR and mass spectra confirm the structure.

EXAMPLE 122

1-(4-Sulphamoylbenzoyl)-2-cyanoaziridine.

A suspension of 2.01 g. 4-sulphamoylbenzoic acid and 0.68 g. 2-cyanoaziridine in 30 ml. tetrahydrofuran is mixed portionwise at ambient temperature with 2 g. dicyclohexylcarbodiimide. The reaction mixture is stirred for 3 hours at ambient temperature, the precipitated dicyclohexylurea (1.4 g.) is filtered off with suction and the filtrate is evaporated in a vacuum. The evaporation residue is dissolved in 70 ml. ethyl acetate, suction filtered to remove 0.3 g. of precipitated material and the ethyl acetate filtrate is shaken with an aqueous solution of sodium bicarbonate and then repeatedly with water. The organic phase, after drying, is evaporated in a vacuum. The evaporation residue (2.1 g.), after trituration with diethyl ether, melts at 162°–165° C. 1.7 g. of this material is boiled with 170 ml. chloroform, 0.55 g. of material melting at 148°–150° C. thereby remaining undissolved. After cooling the chloroform solution, there is obtained a further 0.2 g. of the same material. The 0.75 g. of crystals thus obtained, which melt at 148°–150° C., is again boiled with 70 ml. chloroform, whereby, after cooling to ambient temperature, there is obtained 0.65 g. 1-(4-sulphamoylbenzoyl)-2-cyanoaziridine; m.p. 145°–146° C.

EXAMPLE 123.

1-Sorboyl-2-cyanoaziridine.

A solution of 2.6 g. sorbic acid chloride (b.p. 73° C./12 mm. Hg, obtained from sorbic acid by reaction with thionyl chloride in benzene) is added dropwise at 0° C. to a solution of 1.38 g. 2-cyanoaziridine and 2.4 g. triethylamine in 30 ml. diethyl ether. The reaction mixture is stirred for 1 hour at 0° C. and for 2 hours at ambient temperature, the precipitated hydrochloride (2.68 g.) is filtered off with suction, the ethereal filtrate is repeatedly shaken out with aqueous sodium bicarbonate solution and the ethereal phase is evaporated to give 2.72 g. of evaporation residue. 1 g. of this is purified on a silica gel column (200 g. silica gel, elution agent toluene/dioxan 9:1 v/v) to give 0.75 g. 1-sorboyl-2-cyanoaziridine; m.p. 56°–58° C.

EXAMPLE 124

1-(Rhodanine-N-methylcarbonyl)-2-cyanoaziridine.

A solution of 0.95 g. rhodanine-N-acetic acid in 30 ml. diethyl ether is added dropwise at ambient temperature to a solution of 0.34 g. of 2-cyanoaziridine and 1.06 g. dicyclohexylcarbodiimide in 20 ml. diethyl ether. The reaction mixture is stirred for 3 hours at ambient temperature and the precipitated crystals (1.8 g.) are filtered off with suction and stirred with 10 ml. ethyl acetate. After evaporation thereof in a vacuum, there is obtained 0.6 g. 1-(rhodanine-N-methylcarbonyl)-2-cyanoaziridine in the form of an orange-colored, viscous oil which still contains a small amount of ethyl acetate. The substance cannot be kept very long at ambient temperature. The elementary analysis and the IR, NMR and mass spectra confirm the structure.

EXAMPLE 125

1-(5-Phenylhydantoyl)-2-cyanoaziridine.

A suspension of 1.94 g. N-phenyl-N'-carboxymethylurea (m.p. 195°–197° C.) and 0.68 g. 2-cyanoaziridine in 40 ml. diethyl ether is mixed dropwise, with stirring, with a solution of 2 g. dicyclohexylcarbodiimide in 20 ml. diethyl ether. The reaction mixture is stirred for 4 hours at ambient temperature and then left to stand overnight. The solid product obtained is filtered off with suction (3.6 g.), washed with diethyl ether, triturated with 100 ml. ethyl acetate and dicyclohexylurea (m.p. 225°–227° C.) is filtered off with suction. The filtrate is washed with a saturated aqueous solution of sodium bicarbonate and then a few times with water, the organic phase is dried and the ethyl acetate solution is evaporated in a vacuum. The solid evaporation residue is triturated with diethyl ether to give 1.1 g. 1-(5-phenylhydantoyl)-2-cyanoaziridine (m.p. 114°–116° C.), which still contains a small amount of 3-phenylhydantoin and dicyclohexylurea.

EXAMPLE 126

1-(4-Acetamidomethyl-1-cyclohexane-carbonyl)-2-cyanoaziridine.

A solution of 4 g. dicyclohexylcarbodiimide in 20 ml. tetrahydrofuran is added dropwise at ambient temperature to 3.94 g. trans-4-acetamidomethylcyclohexane-1-carboxylic acid (m.p. 143°–152° C.) and 1.36 g. 2-cyanoaziridine and 80 ml. tetrahydrofuran. The reaction mixture is stirred for 4 hours at ambient temperature and then left to stand overnight. The solid material (5.6 g.) is now filtered off with suction, washed with tetrahydrofuran and diethyl ether into the filtrate and this is evaporated in a vacuum, 4.18 g. of an oil remaining behind. This oil is dissolved in ethyl acetate, the solution obtained is shaken with a saturated aqueous solution of sodium bicarbonate and subsequently a few times with water and the organic phase is evaporated. The oily evaporation residue (3.3 g.) is repeatedly triturated with diethyl ether to give 1.8 g. of product (m.p. 97°–100° C.) which, after trituration with about 50 ml. ethyl acetate, gives 0.5 g. of undissolved material (m.p. 190°–193° C.), whereas the filtrate, after evaporation in a vacuum and trituration of the evaporation residue with diethyl ether, gives 1 g. (1-(4-acetamidomethyl-1-cyclohexane-carbonyl)-2-cyanoaziridine; m.p. 92°–94° C.

EXAMPLE 127

1-(1-p-Chlorophenylcyclopentane-1-carbonyl)-2-cyanoaziridine.

A solution of 2.43 g. 1-(4-chlorophenyl)-1-cyclopentane-carboxylic acid chloride (b.p. 176°–178° C./12 mm. Hg) in 40 ml. diethyl ether is added dropwise at 0° to 5° C. to a mixture of 0.68 g. 2-cyanoaziridine and 1.2 g. triethylamine in 40 ml. diethyl ether. The reaction mixture is stirred for 1 hour at 0° C. and for 2 hours at ambient temperature. The precipitated hydrochloride (1.35 g.) is filtered off with suction and the filtrate is shaken with an aqueous solution of sodium bicarbonate and repeatedly with water. The ethereal phase is dried and evaporated to give 2.5 g. of an oil which solidifies after standing for some time. There are thus obtained 2.5 g. (1-(1-p-chlorophenylcyclopentane-1-carbonyl)-2-cyanoaziridine; m.p. 80°–82° C.

EXAMPLE 128

Cyclohexane-1,2-dicarbonyl-bis-1-(2-cyanoaziridine).

A solution of 4.1 g. dicyclohexylcarbodiimide in 20 ml. diethyl ether is added dropwise to a suspension of 1.72 g. cis-cyclohexane-1,2-dicarboxylic acid and 1.38 g. 2-cyanoaziridine in 30 ml. diethyl ether. The reaction mixture is stirred for 2 hours at ambient temperature, left to stand overnight and the resultant dicyclohexylurea (m.p. 227°–230° C.) is filtered off with suction. The ethereal filtrate is repeatedly shaken with water and the ethereal phase is evaporated to give 3.02 g. of a yellow oil. This is purified on a silica gel column (600 g. silica gel; elution agent toluene/dioxan 8:2 v/v). There is thus obtained 1.02 g. cyclohexane-1,2-dicarbonyl-bis-1-(2-cyanoaziridine) in the form of a viscous, water clear oil which still contains a little water and dioxan. The elementary analysis and the IR, NMR and mass spectra confirm the structure.

EXAMPLE 129

1-(3-Camphorcarbonyl)-2-cyanoaziridine.

A solution of 2 g. dicyclohexylcarbodiimide in 20 ml. diethyl ether is added dropwise at ambient temperature to a solution of 1.96 g. DL-3-camphor-carboxylic acid and 0.68 g. 2-cyanoaziridine in 60 ml. diethyl ether. The reaction mixture is stirred for 3 hours and then left to stand overnight. The resultant dicyclohexylurea (2.18 g.) is filtered off with suction and the filtrate is concentrated to a volume of about 50 ml. and left to stand overnight in a refrigerator, a further 0.03 g. dicyclohexylurea thereby precipitating out. This is filtered off with suction and the filtrate is evaporated in a vacuum, finally in a high vacuum, to give 2.44 g. 1-(3-camphorcarbonyl)-2-cyanoaziridine in the form of a cololess, viscous oil which contains a small amount of 3-camphorcarboxylic acid. The elementary analysis and the IR, NMR and mass spectra confirm the structure.

EXAMPLE 130

1-(3-Acetylpropionyl)-2-cyanoaziridine.

A solution of 6 g. dicyclohexylcarbodiimide in 45 ml. diethyl ether is added dropwise at ambient temperature to a solution of 3.48 g. laevulinic acid and 2.04 g. 2-cyanoaziridine in 90 ml. diethyl ether. The reaction mixture is stirred for 5 hours at ambient temperature, left to stand overnight and the resultant dicyclohexylurea (5.7 g.; m.p. 226°–228° C.) filtered off with suction. The filtrate is evaporated to about one third of its volume, shaken once with an aqueous solution of sodium bicarbonate and twice with water and the ethereal phase evaporated, 4.3 g. of an oil remaining behind. The aqueous phase is immediately repeatedly extracted with ethyl acetate and the combined ethyl acetate extracts are evaporated in a vacuum, 1.2 g. of an oil remaining behind, which mainly consists of the desired product and 2-cyanoaziridine. The oil from the ether evaporation residue (4.3 g.) is left to stand for some days in a refrigerator, a smeary crystallizate forming which is repeatedly triturated with about 10 ml. water. 1.05 g. of crystals with a melting point of 93° to 94° C. thus remain which is N-3-acetylpropionyldicyclohexylurea. The combined aqueous filtrates thereof are immediately repeatedly extracted with ethyl acetate and the combined ethyl acetate extracts are evaporated in a vacuum. There are obtained 2.8 g. of the desired product in the form of a colorless oil. The elementary analysis and the IR, NMR and mass spectra confirm the structure of the product.

EXAMPLE 131

Thiodiglycolyl-bis-1-(2-cyanoaziridine).

A solution of 3 g. thiodiglycolic acid, 8.6 g. dicyclohexylcarbodiimide and 2.7 g. 2-cyanoaziridine in 60 ml. tetrahydrofuran is stirred for 2 hours in an ice bath. After separating off the precipitated dicyclohexylurea, the product obtained is purified on a column of silica gel, using ethyl acetate as elution agent, to give 2.5 g. thiodiglycolyl-bis-1-(2-cyanoaziridine) in the form of a colorless oil.

EXAMPLE 132

Diglycolyl-bis-(2-cyanoaziridine).

This compound, which is obtained from 1.34 g. diglycolic acid in the above-described manner, is recrystallized from ethyl acetate/diethyl ether. The yield is 0.75 g., and the product melts at 112° C.

EXAMPLE 133

1-(11-Acetylaminoundecanoyl)-2-cyanoaziridine.

In a manner analogous to that described above, from 2.43 g. 11-acetaminoundecanoic acid, there is obtained 0.85 g. 1-(11-acetylaminoundecanoyl)-2-cyanoaziridine in the form of an oil which can be crystallized from diethyl ether and then melts at 62° to 65° C.

EXAMPLE 134

Benzenephosphono-bis-1-(2-cyanoaziridine).

3 g. 2-Cyanoaziridine and 6.1 ml. triethylamine are dissolved in 120 ml. dioxan. 3.9 g. Benzenephosphonic acid dichloride are then added dropwise thereto, the reaction mixture is left to stand overnight and the precipitated salt is separated off. The evaporation residue is purified on a silica gel column, using dioxan as elution agent. After treatment with ligroin, there is obtained 0.85 g. benzenephosphono-bis-1-(2-cyanoaziridine) in the form of crystals which melt at 116°–121° C.

EXAMPLE 135

Ethoxyphosphoryl-bis-1-(2-cyanoaziridine).

2.7 g. 2-Cyanoaziridine and 5.6 ml. triethylamine are dissolved in 26 ml. anhydrous diethyl ether. 3.2 g. Phosphoric acid ethyl ester dichloride dissolved in 32 ml. anhydrous diethyl ether are added dropwise thereto, with ice cooling. After standing overnight at ambient temperature, the precipitated salt is separated off and 2.3 g. ethoxyphosphoryl-bis-1-(2-cyanoaziridine) are obtained in the form of a yellowish oil.

EXAMPLE 136

1-(Phenoxyhydroxyphosphoryl)-2-cyanoaziridine.

1.74 g. Phosphoric acid monophenyl ester and 1.39 ml. triethylamine are suspended in 17.4 ml. tetrahydrofuran. After the addition of 0.68 g. 2-cyanoaziridine, a clear solution is formed which is mixed, in an ice bath, with 2.16 g. dicyclohexylcarbodiimide. After 2 hours, the precipitated dicyclohexylurea is separated off and the filtrate is evaporated to give 2.4 g. of the triethylammonium salt as a yellowish oil.

EXAMPLE 137

Dithiodiacetyl-bis-1-(2-cyanoaziridine).

3.6 g. Dithiodiacetic acid are dissolved in 72 ml. diethyl ether, cooled and 2.7 g. 2-cyanoaziridine, as well as 8.6 g. dicyclohexylcarbodiimide, are added thereto. After 2 hours, precipitated dicyclohexylurea is separated off and the filtrate is evaporated. The evaporation residue is purified on a silica gel column with xylene/methyl ethyl ketone. There are thus obtained 2.2 g. dithiodiacetyl-bis-1-(2-cyanoaziridine) in the form of a yellowish oil.

EXAMPLE 138

(R)(−)-1-(α-Methoxyphenylacetyl)-2-cyanoaziridine.

1 g. (R)(−)-2-Methoxy-2-phenylacetic acid are dissolved in 10 ml. diethyl ether. 1.3 g. Dicyclohexylcarbodiimide is added thereto with ice cooling and, after 15 minutes, 0.4 g. 2-cyanoaziridine in 2 ml. diethyl ether. After 2 hours in an ice bath, the precipitated dicyclohexylurea is separated off and the filtrate is evaporated to give 1.2 g. (R)(−)-1-(α-methoxyphenylacetyl)-2-cyanoaziridine in the form of an oil; $[\alpha]_D^{20} = -99.0°$ (c=0.5 in ethanol).

(S)(+)-1-(α-Methoxyphenylacetyl)-2-cyanoaziridine.

Starting from (S)(+)-2-methoxy-2-phenylacetic acid, there is obtained, in an analogous manner, the optical antipode which is also in the form of an oil; $[\alpha]_D^{20} = +89.9°$ (c=0.5 in ethanol).

EXAMPLE 139

1-N-Mesylglycyl-2-cyanoaziridine.

A suspension of 3 g. N-mesylglycine in 30 ml. diethyl ether is stirred for 2 hours in an ice bath with 1.36 g. 2-cyanoaziridine and 4.32 g. dicyclohexylcarbodiimide. The precipitated dicyclohexylurea is filtered off and the filtrate evaporated. The evaporation residue is recrystallized from ethyl acetate/ligroin finally to give 1.17 g. 1-N-mesylglycyl-2-cyanoaziridine in the form of white crystals; m.p. 83°–88° C.

EXAMPLE 140

Benzenethiophosphono-bis-1-(2-cyanoaziridine).

1.36 g. 2-Cyanoaziridine and 2.78 ml. triethylamine are dissolved in 27 ml. anhydrous ether. A solution of 2.11 g. benzenethiophosphonic acid dichloride in 21 ml. anhydrous diethyl ether is added dropwise thereto at 0° to 5° C. After 2 hours, the precipitated salt is filtered off, the filtrate is evaporated and the residue is purified on a silica gel column using ethyl acetate as elution agent. There is thus obtained 1.75 g. benzenethiophosphono-bis-1-(2-cyanoaziridine) in the form of a yellowish oil.

EXAMPLE 141

Phenoxyphosphoryl-bis-1-(2-cyanoaziridine).

5.4 g. 2-Cyanoaziridine and 11.1 ml. triethylamine are introduced into 108 ml. anhydrous diethyl ether. 8.4 g. Phenoxyphosphoryl dichloride in 84 ml. anhydrous diethyl ether are added dropwise thereto at 5° to 10° C. After 1.5 hours, precipitated salt is separated off and the product is purified on a silica gel column with ethyl acetate as elution agent. There is obtained 0.7 g. phenoxyphosphoryl-bis-1-(2-cyanoaziridine); m.p. 81°–88° C.

EXAMPLE 142

1-(Diphenylaminophosphoryl)-2-cyanoaziridine.

2.67 g. Phosphoric acid dianilide chloride in the tenfold amount of anhydrous tetrahydrofuran is added, with ice cooling, to a solution of 0.68 g. 2-cyanoaziridine and 1.38 ml. triethylamine in 13.6 ml. tetrahydrofuran. After 2 hours, the precipitated salt is separated off and the filtrate is evaporated. After stirring with ethyl acetate, there is obtained 1.26 g. 1-(diphenylaminophosphoryl)-2-cyanoaziridine; m.p. 169°–172° C.

EXAMPLE 143

1-(Benzenemethoxyphosphonyl)-2-cyanoaziridine.

This compound is obtained in a yield of 1.9 g. in the form of a pale yellow oil in an analogous manner from 5 g. benzenemethoxyphosphonic acid chloride.

EXAMPLE 144

1-Dimethoxyphosphoryl-2-cyanoaziridine.

This compound is obtained in an analogous manner in the form of an oil from phosphoric acid dimethyl ester chloride. The spectral analyses confirm the structure.

EXAMPLE 145

1-(3-Methylthiopyridazine-6-carbonyl)-2-cyanoaziridine.

2.2 g. 3-Carboxy-6-methylthiopyridazine are suspended in 22 ml. diethyl ether, mixed with 0.88 g. 2-cyanoaziridine and 2.8 g. dicyclohexylcarbodiimide and then stirred for 2 hours in an ice bath. After standing overnight at ambient temperature, the thick suspension is filtered with suction, evaporated and purified over a silica gel column using ethyl acetate as elution agent. There is obtained 0.4 g. 1-(3-methylthiopyridazine-6-carbonyl)-2-cyanoaziridine; m.p. 97°–100° C.

EXAMPLE 146

1-[N-(Pyridine-2-carbonyl)-glycyl]-2-cyanoaziridine.

3.6 g. N-(Pyridine-2-carbonyl)-glycine are suspended in 36 ml. tetrahydrofuran, 1.36 g. 2-cyanoaziridine and 4.3 g. dicyclohexylcarbodiimide are added thereto and the reaction mixture is stirred for 2 hours in an ice bath. After filtering off the dicyclohexylurea and working up, there are obtained 2.85 g. 1-[N-(pyridine-2-carbonyl)-glycyl]-2-cyanoaziridine in the form of a yellowish oil.

EXAMPLE 147

1-(Ethanemethoxyphosphonyl)-2-cyanoaziridine.

1.29 g. 2-Cyanoaziridine are dissolved in 13 ml. anhydrous diethyl ether, 2.63 ml. triethylamine are added thereto and then 2.7 g. ethanemethoxyphosphonic acid chloride are added thereto dropwise, with ice cooling.

After 3 days, the precipitated triethylamine hydrochloride is filtered off. After working up, there are obtained 2.95 g. 1-(ethanemethoxyphosphonyl)-2-cyanoaziridine in the form of a water-soluble, yellowish oil.

EXAMPLE 148

1-[N-α-(L)-Phenethylsuccinamoyl]-2-cyanoaziridine.

2.21 g. N-α-(L)-Phenethylsuccinic acid semiamide, 0.68 g. 2-cyanoaziridine and 2.16 g. dicyclohexylcarbodiimide in 22 ml. tetrahydrofuran are stirred for 2 hours in an ice bath. After standing overnight, the precipitated dicyclohexylurea is filtered off. After working up, there is obtained 1-[N-α-(L)-phenethylsuccinamoyl]-2-cyanoaziridine in the form of a yellowish oil; $[\alpha]_D^{20} = -94.2°$ (c=0.5 in ethanol).

EXAMPLE 149

1-[N-α-(D)-Phenethylsuccinamoyl]-2-cyanoaziridine.

This is prepared in an analogous manner from the D-acid. The product is a yellowish oil; $[\alpha]_D^{20} = +92.0°$ (c=0.5 in ethanol).

EXAMPLE 150

1-(N-Acetylglycyl)-2-cyanoaziridine 11.7 g. N-acetylglycine are introduced in 400 ml. anhydrous methylene chloride and 11.5 ml. N-methylmorpholine is added. After cooling in an ice bath a solution of 13.8 ml. isobutyl chloroformate in 100 ml. anhydrous methylene chloride and 15 minutes later a solution of 6.8 g. 2-cyanoaziridine in anhydrous methylene chloride are added and then stirred for 2 hours in an ice bath. After standing overnight at ambient temperature the solution is evaporated in a vacuum, the residue is triturated with acetone and the N-methylmorpholine hydrochloride, which remains undissolved, is filtered off with suction. The acetone solution is evaporated in a vacuum and the residue is recrystallized from diethyl ether/methanol (1:1). The yield is 8.4 g. of a white, clear water-soluble crystallized product, which is not only identical with the compound of example 30, but also with the reaction compound of 2-cyanoaziridine and N-acetylglycyl chloride in an ethyl acetate solution in the presence of triethylamine.

The pharmacological properties of the new compounds were determined as follows:

Adult female Sprague-Dawley rats of Messrs. WIGA (Gassner, Sulzfeld) weighing 180–220 g were used. The animals were kept at a constant temperature (23°±1° C.), constant humidity of the atmosphere (55±5%) and within the 12-hour day/night rhythm. The animals received rat pellets SNIFF of Messrs. Intermast, Soest, and water ad libitum. The substances to be tested (dissolved in 10 ml of 0.5% tylose solution per kg of body weight) were once orally applied to 10 rats each time, by means of a throat tube. As control, 10 animals each time were only treated with 10 ml of 0.5% tylose solution per kg of body weight. Prior to the application, the animals were kept fasting and blood was taken from the retroorbital venous plexus by means of a heparinized puncture capillary tube (B 3095/2 of Messrs. Sherwood Med. Inc., Inc., St. Louis) and the leucocytes were determined by means of a Coulter counter in known manner.

On the 4th day blood was again taken from the retroorbital venous plexus and the leucocytes were counted. The averages with standard deviations were ascertained from the individual values. The test groups were only evaluated if the control groups showed no physiological variations. Table 1 shows the values in comparison with the 1-carboxamido-2-cyanoaziridine (BA 1).

The following data show that all tested substances effect significant increase of the leucocyte number and thus are strongly immune-stimulating.

TABLE

| Active Material of Example | Per os Dosage mg/kg | Leucocytes in Thousands 0-Value | Maximum (after 4 days) |
|---|---|---|---|
| Comparison BA 1 | 200 | 8.9 | 9.5 |
| 2 | 200 | 6.4 | 12.5 |
| 3 | " | 5.6 | 15.6 |
| 4 | " | 6.6 | 12.1 |
| 13 | " | 6.4 | 12.4 |
| 14 | " | 6.7 | 14.3 |
| 19 | " | 6.8 | 10.7 |
| 20 | " | 7.2 | 9.9 |
| 23 | " | 8.1 | 15.2 |
|  | 50 | 7.2 | 10.9 |
| 25 | 200 | 7.6 | 16.0 |
| 27 | " | 6.8 | 14.0 |
| 29 | " | 6.4 | 12.5 |
| 30 | " | 6.8 | 18.0 |
|  | 50 | 6.6 | 10.2 |
| 31 | 200 | 8.6 | 16.8 |
|  | 50 | 7.8 | 10.2 |
| 35 | 200 | 8.0 | 14.7 |
|  | 50 | 8.0 | 11.6 |
| 38 | 200 | 6.4 | 12.5 |
| 39 | " | 6.9 | 13.5 |
| 41 | " | 6.7 | 13.8 |
| 42 | " | 5.6 | 10.1 |
| 44 | " | 8.5 | 16.4 |
| 47 | " | 7.7 | 13.7 |
| 54 | " | 5.7 | 15.6 |
| 60 | " | 8.0 | 15.4 |
| 63 | 200 | 7.0 | 13.7 |
| 66 | " | 5.6 | 10.3 |
| 69 | " | 5.8 | 11.4 |
| 73 | " | 7.1 | 11.7 |
| 76 | " | 6.3 | 11.3 |
| 83 | " | 5.2 | 12.3 |
| 86 | " | 4.7 | 11.8 |
| 88 | " | 5.2 | 10.0 |
| 89 | " | 5.8 | 14.7 |
| 91 | " | 5.9 | 9.7 |
| 94 | " | 6.0 | 11.6 |
| 95 | " | 4.9 | 10.2 |
| 96 | " | 5.4 | 11.5 |
| 97 | " | 6.0 | 13.5 |
| 99 | " | 6.3 | 13.6 |
| 102 | " | 6.4 | 10.9 |
| 105 | " | 4.4 | 11.3 |
| 107 | " | 5.5 | 9.9 |
| 109 | " | 6.0 | 10.8 |
| 110 | " | 6.1 | 10.3 |
| 119 | " | 7.0 | 12.0 |
| 122 | " | 7.3 | 12.5 |
| 123 | " | 6.0 | 10.1 |
| 131 | " | 5.4 | 11.7 |
| 132 | " | 5.6 | 13.7 |
| 134 | " | 5.9 | 12.2 |
| 135 | " | 6.4 | 12.1 |
| 136 | " | 5.0 | 9.8 |
| 140 | " | 5.3 | 9.4 |
| 143 | " | 5.9 | 10.1 |
| 149 | " | 4.2 | 8.5 |

The present invention also provides pharmaceutical compositions comprising the new compound and/or at least one solid or liquid pharmaceutical diluent or carrier.

For the preparation of pharmaceutical compositions, a 1-acyl-2-cyanoaziridine in accordance with the invention is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatin, agar-agar, calcium phosphate, magnesium stearate, animal and vegetable fats and solid high molecular weight poylmers (such as polyethylene glycols). Compositions suitable for oral administration can, if desired, contain flavoring and/or sweetening materials.

However, the active material is preferably injected. As injection medium, it is preferred to use water which contains the additives usual in the case of injection soultions, such as stabilizing agents, solubilizing agents and/or weakly alkaline buffers. Additives of this type include, for example, phosphate and carbonate buffers, ethanol, complex-forming agents (for example ethylenediamine-tetraacetic acid and the non-toxic salts thereof) and high molecular weight polymers (for example liquid polyethylene oxide) for viscosity regulation.

For treatment of humans the active material may be applied one or more times with each dose containing about 25 to 3000 and preferably 50 to 500 mg of active material.

It will be appreciated that the instant specification and examples are set forth by way of illustration and not limitation, and that various modifications and changes may be made without departing from the spirit and scope of the present invention.

What we claim is:

1. A 1-acyl-2-cyanoaziridine of the formula

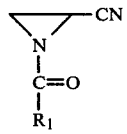

in which $R_1$ is
(a) a cyclic aliphatic hydrocarbon radical with 3 to 7 carbon atoms,
(b) a straight-chained or branched hydrocarbon radical with 1 to 5 carbon atoms which is mono- or di-substituted by
 (1) a carbamoyl optionally mono- or di-substituted by a lower alkyl group,
 (2) a lower alkoxy carbonyl,
 (3) a lower alkoxy or a lower alkylthio substituted by a radical or the formula

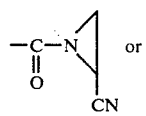

(4) an acylamino group of the formula

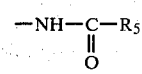

in which $R_5$ is hydrogen, lower alkoxy, vinyl or lower alkyl,
(c) a phenyl group which is substituted by a phenyl group,

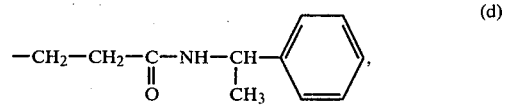

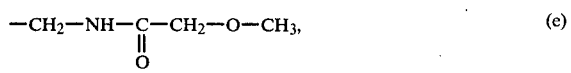

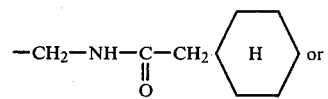

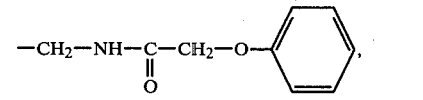

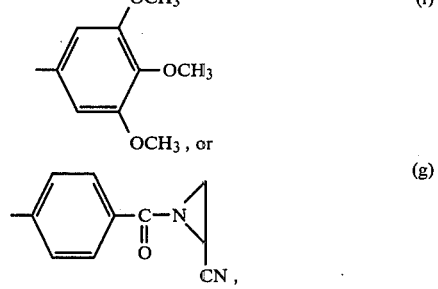

or a pharmacologically compatible salt thereof.

2. A compound according to claim 1 wherein such compound is thiodiglycolyl-bis-1-(2-cyanoaziridine) or a pharmacologically compatible salt thereof.

3. An immune-stimulating composition of matter consisting essentially of an immune-stimulating effective amount of a compound or salt according to claim 1 in combination with a pharmacologically compatible diluent.

4. The method of stimulating an immune response in a patent comprising administering to the patient an immune-stimulating effective amount of a composition according to claim 3.

5. The method of increasing the number of leucocytes in the system of a patient comprising administering to the patient a leucocyte-increasing effective amount of a composition according to claim 3.

6. A compound according to claim 1 wherein such compound is 1-(N,N-diethylsuccinamoyl)-2-cyanoaziridine or a pharmacologically compatible salt thereof.

7. A compound according to claim 1 wherein such compound is 1-cyclopropylcarbonyl-2-cyanoaziridine or a pharmacologically compatible salt thereof.

8. A compound according to claim 1 wherein such compound is 1-(3,4,5-trimethoxybenzoyl)-2-cyanoaziridine or a pharmacologically compatible salt thereof.

9. A compound according to claim 1 wherein such compound is 1-acryloylamidoacetyl-2-cyanoaziridine or a pharmacologically compatible salt thereof.

10. A compound according to claim 1 wherein such compound is N,N'-terephthaloyl-bis-1-(2-cyanoaziridine) or a pharmacologically compatible salt thereof.

11. A compound according to claim 1 wherein such compound is 1-(p-phenylbenzoyl)-2-cyanoaziridine or a pharmacologically compatible salt thereof.

12. A compound according to claim 1 wherein such compound is diglycolyl-bis-(2-cyanoaziridine) or a pharmacologically compatible salt thereof.

13. A compound according to claim 1 wherein such compound is 1-[N-α-(D)-phenethylsuccinamoyl]-2-cyanoaziridine or a pharmacologically compatible salt thereof.

14. A compound according to claim 1 wherein such compound is 1-cyclohexylacetamidoacetyl-2-cyanoaziridine or a pharmacologically compatible salt thereof.

15. A compound according to claim 1 wherein such compound is 1-phenoxyacetamidoacetyl-2-cyanoaziridine or a pharmacologically compatible salt thereof.

16. A compound according to claim 1 wherein such compound is 1-methoxysuccinyl-2-cyanoaziridine or a pharmacologically compatible salt thereof.

17. A compound according to claim 1 wherein such compound is 1-succinamoyl-2-cyanoaziridine or a pharmacologically compatible salt thereof.

18. A compound according to claim 1 wherein such compound is 1-(N-acetylglycyl)-2-cyanoaziridine or a pharmacologically compatible salt thereof.

19. A compound according to claim 1 wherein such compound is 1-(N-formylglycly)-2-cyanoaziridine or a pharmacologically compatible salt thereof.

20. A compound according to claim 1 wherein such compound is 1-(N-ethoxycarbonylglycyl)-2-cyanoaziridine or a pharmacologically compatible salt thereof.

21. A compound according to claim 1 wherein such compound is 1-(N-acetyl-D-alanyl)-2-cyano(D- and L-) aziridine or a pharmacologically compatible salt thereof.

22. A compound according to claim 1 wherein such compound is 1-(N-methoxyacetylglycyl)-2-cyanoaziridine or a pharmacologically compatible salt thereof.

23. A compound according to claim 1 wherein such compound is 1-(6-acetylaminohexanoyl)-2-cyanoaziridine or a pharmacologically compatible salt thereof.

24. A compound according to claim 1 wherein such compound is 1-cyclohexylcarbonyl-2-cyanoaziridine or a pharmacologically compatible salt thereof.

* * * * *